US008370076B2

(12) United States Patent
Chen et al.

(10) Patent No.: US 8,370,076 B2
(45) Date of Patent: Feb. 5, 2013

(54) COMPUTER METHOD AND SYSTEM FOR PREDICTING PHYSICAL PROPERTIES USING A CONCEPTUAL SEGMENT-BASED IONIC ACTIVITY COEFFICIENT MODEL

(75) Inventors: Chau-Chyun Chen, Lexington, MA (US); Yuhua Song, Somerville, MA (US)

(73) Assignee: Aspen Technology, Inc., Burlington, MA (US)

( * ) Notice: Subject to any disclaimer, the term of this patent is extended or adjusted under 35 U.S.C. 154(b) by 123 days.

(21) Appl. No.: 12/859,542

(22) Filed: Aug. 19, 2010

(65) Prior Publication Data
US 2011/0046936 A1 Feb. 24, 2011

Related U.S. Application Data

(60) Division of application No. 11/241,675, filed on Sep. 30, 2005, now Pat. No. 7,809,540, which is a continuation-in-part of application No. 10/785,925, filed on Feb. 24, 2004, now Pat. No. 7,672,826.

(51) Int. Cl.
*G01N 33/48* (2006.01)
*G06G 7/48* (2006.01)
*G06G 7/58* (2006.01)
*G01N 31/00* (2006.01)

(52) U.S. Cl. ............... 702/19; 702/22; 703/11; 703/12

(58) Field of Classification Search .................. None
See application file for complete search history.

(56) References Cited

U.S. PATENT DOCUMENTS

| 5,687,090 | A  | 11/1997 | Chen et al. |
| 6,311,093 | B1 | 10/2001 | Brown |
| 6,311,095 | B1 | 10/2001 | Brown |
| 6,662,061 | B1 | 12/2003 | Brown |
| 6,766,817 | B2 | 7/2004  | Da Silva |
| 6,918,404 | B2 | 7/2005  | Da Silva |
| 7,066,586 | B2 | 6/2006  | Da Silva |
| 2005/0187748 | A1 | 8/2005 | Chen et al. |

FOREIGN PATENT DOCUMENTS

EP 0463694 A2 1/1992

OTHER PUBLICATIONS

Ahamed, T., et al., "A Generalized Approach to Thermodynamic Properties of Biomolecules for Use in Bioseparation Process Design," *Fluid Phase Equilibria*, 241:268-282 (2006).
Anderko, A., et al., "Electrolyte Solutions from Thermodynamic and Transport Property Models to the Simulation of Industrial Processes," *Fluid Phase Equilibria*, 194-197:123-142 (2002).
Beerbower, A., et al., "Expanded Solubility Parameter Approach I: Naphthalene and Benzoic Acid in Individual Solvents," *Journal of Pharmaceutical Sciences*, 73(2):179-188 (1984).
Bustamante, P., et al., "The Modified Extended Hansen Method to Determine Partial Solubility Parameters of Drugs Containing a Single Hydrogen Bonding Group and their Sodium Derivatives: Benzoic Acid/Na and Ibuprofen/Na," *International Journal of Pharmaceutics*, 194:117-124 (2000).
Chen, C.C. and Crafts, P.A., "Correlation and Prediction of Drug Molecule Solubility in Mixed Solvent Systems with the Nonrandom Two-Liquid Segment Activity Coefficient (NRTL-SAC) Model," *Ind, Eng. Chem. Res.*, 45:4816-4824 (2006).
Chen, C.C. and Mathias, P.M., "Applied Thermodynamics for Process Modeling," *AIChE Journal*, 48(2): 194-200 (2002).
Chen, C.C. and Song, Y., "Extension of Nonrandom Two-Liquid Segment Activity Coefficient Model for Electrolytes," *Ind. Eng. Chem. Res.*, 44(23):8909-8921 (2005).
Chen, C.C. and Song, Y., "Generalized Electrolyte-NRTL Model for Mixed-Solvent Electrolyte Systems," *AIChE Journal*, 50(8):1928-1941 (2004).
Chen, C.C. and Song, Y., "Solubility Modeling with a Nonrandom Two-Liquid Segment Activity Coefficient Model," *Ind. Eng. Chem. Res.*, 43(26):8354-8362 (2004).
Chen, C.C., "A Segment-Based Local Composition Model for the Gibbs Energy of Polymer Solutions," *Fluid Phase Equilibria*, 83:301-312 (1993).
Chen, C.C., "Molecular Thermodynamic Model for Gibbs Energy of Mixing of Nonionic Surfactant Solutions," *AIChE Journal*, 42(11):3231-3240 (1996).
Chen, C.C., et al., "Local Composition Model for Excess Gibbs Energy of electrolyte Systems," *AIChE Journal*, 28(4):588-596 (1982).
Chen, C.C., et al., "Segment-Based Excess Gibbs Energy Model for Aqueous Organic Electrolytes," *AIChE Journal*, 47(11):2593-2602 (2001).
Chen, C.C., et al., "Use of Hydration and Dissociation Chemistries with the Electrolyte-NRTL Model," *AIChE Journal*, 45(7):1576-1586 (1999).
Frank, T.C. et al., "Quickly Screen Solvents for Organic Solids," *Chemical Engineering Progress*, pp. 41-66 (1999).
Fredenslund, A., et al., "Group-Contribution Estimation of Activity Coefficients in Nonideal Liquid Mixtures," *AIChE Journal*, 21(6):1086-1099 (1975).
Gracin, S. and Rasmuson, A.C., "Solubility of Phenylacetic Acid, p-Hydroxyphenylacetic Acid, p-Aminophenylacetic Acid, p-Hydroxybenzoic Acid, and Ibuprofen in Pure Solvents," *J. Chem. Eng. Data*, 47:1379-1383 (2002).
Hansen, C.M., "Hansen Solubility Parameters a User's Handbook," *CRC Press* (2000).
J. Barra, et al., "Proposition of Group Molar Constants for Sodium to Calculate the Partial Solubility Parameters of Sodium Salts Using the Van Krevelen Group Contribution Method," *European Journal of Pharmaceutical Sciences*, 10:153-161 (2000).

(Continued)

Primary Examiner — Eric S DeJong
(74) Attorney, Agent, or Firm — Hamilton, Brook, Smith & Reynolds, P.C.

(57) ABSTRACT

In the present invention the NonRandom Two-Liquid segment activity coefficient model system of the parent application is extended for computation of ionic activity coefficients and solubilities of electrolytes, organic and inorganic, in common solvents and solvent mixtures. The invention method and system may be applied to the chemical and/or pharmaceutical design process. In addition to the three types of molecular parameters defined for organic nonelectrolytes, i.e., hydrophobicity X, polarity Y, and hydrophilicity Z, an electrolyte parameter, E, is introduced to characterize both local and long-range ion-ion and ion-molecule interactions attributed to ionized segments of electrolytes. Successful representations of mean ionic activity coefficients and solubilities of electrolytes, inorganic and organic, in aqueous and nonaqueous solvents are presented.

13 Claims, 21 Drawing Sheets

OTHER PUBLICATIONS

Lipinski, et al., "Experimental and Computational Approaches to Estimate Solubility and Permeability in Drug Discovery and Development Settings," *Advanced Drug Delivery Reviews*, 23:3-25 (1997).

Miller, J.M., Chromatography, Concepts and Contrasts. $2^{nd}$ Ed. New Jersey: Wiley-Interscience Publication, John Wiley & Sons, Inc., 2005.

Park, J.H., et al., "UNIFAC Model as a Heuristic Guide for Estimating Retention in Reversed-Phased Liquid Chromatography," *J. of Chromatography A*, 656:69 (1993).

Park, J.H., et al., "UNIFAC Model as a Heuristic Guide for Estimating Retention in Chromatography," *J. of Chromatography*, 586:1-9 (1991).

Pitzer, K.S., "Electrolytes, from Dilute Solutions to Fused Salts," *Journal of the American Chemical Society*, 102(9):2902-2906 (1980).

Pitzer, K.S., "Thermodynamics of Electrolytes. I. Theoretical Basis and General Equations," *The Journal of Physical Chemistry*, 77(2):267-277 (1973).

Rashin, A.A. and Honig, B., "Reevaluation of the Born Model of Ion Hydration," *J. Phys. Chem.*, 89(26):5588-5593 (1985).

Robinson, R.A., D.Sc., Ph.D., F.R.I.C., et al., "Electrolyte Solutions the Measurement and Interpretation of Conductance, Chemical Potential and Diffusion in Solutions of Simple Electrolytes," *Butterworths Scientific Publications* Second Edition (1959).

Snyder, L.R., et al., Practical HPLC Method Development. $2^{nd}$ Ed. New Jersey: Wiley-Interscience Publication, John Wiley & Sons, Inc., 1997.

Stahl P. Heinrich and Wermuth, Camille G., Handbook of Pharmaceutical Salts Properties, Selection, and Use, *International Union of Pure and Applied Chemistry (IUPAC)*, Wiley-VCH, Published Year 2002.

Tung, H.H., et al., "Prediction of Pharmaceuticals Solubility via NRTL-SAC and Cosmo," *VDI Berichte*, 1901(1):271-278 (2005).

Van de Waterbeemd, H. and Gifford, E., "Admet *In Silico* Modeling: Towards Prediction Paradise?," *Nature Publishing Group*, 2:192-204 (2003).

Wang, et al., "A speciation-based model for mixed-solvent electrolyte systems," *Fluid Phase Equilibria*, 203(1-2):141-176 (2002).

Wilczek-Vera, Grazyna, et al., "On the Activity of Ions and the Junction Potential: Revised Values for All Data," *AIChE Journal*, 50(2):445-462 (2004).

US 8,370,076 B2

COMPUTER METHOD AND SYSTEM FOR PREDICTING PHYSICAL PROPERTIES USING A CONCEPTUAL SEGMENT-BASED IONIC ACTIVITY COEFFICIENT MODEL

RELATED APPLICATIONS

This application is a divisional of U.S. application Ser. No. 11/241,675, filed Sep. 30, 2005 now U.S. Pat. No. 7,809,540, which is a continuation-in-part of U.S. application Ser. No. 10/785,925, filed Feb. 24, 2004 now U.S. Pat. No. 7,672,826.

The entire teachings of the above applications are incorporated herein by reference.

BACKGROUND OF THE INVENTION

The chemical and pharmaceutical industries screen and develop hundreds of new chemicals and drug candidates each year. Chemists and engineers are tasked to develop process recipes for these new molecules and the recipes often involve multiple reaction steps coupled with separation steps such as crystallization or extraction. A critical consideration in the chemical process design is the choice of solvents and solvent mixtures, from among hundreds of solvent candidates, for reaction, separation, and purification (Frank, T. C. et al., "Quickly Screen Solvents for Organic Solids," *Chemical Engineering Progress*, December 1999, 41). Phase behavior, especially solubility, of the new molecules in solvents or solvent mixtures weighs heavily in the choice of solvents for recipe development while little if any such experimental data is available for these new molecules. Although limited solubility experiments may be taken as part of the process research and development, during the early stages of development it is typical for limited experimental resource and drug substance availability, to restrict experimental program of solvent selection for process development. Where the process requires a mixed solvent system it is practically impossible to cover the full range of potential solvent combinations with sufficient detail to find the optimal solution, even with modern high throughput techniques. Consequently, solvent selection today is largely dictated by researchers' preferences or prior experiences. This often leads to a sub optimal manufacturing process reaching the pilot plant and potential manufacturability issues at various steps of the process. To overcome these obstacles, it is highly desirable to have a predictive model of chemical solubility in single and mixed solvent systems, based on a small initial set of measured solubilities.

Existing solubility parameter models such as that of Hansen (Hansen, C. M., *Hansen Solubility Parameters: A User's Handbook*; CRC Press, 2000) offer very limited predictive power while group contribution models such as UNIFAC (Fredenslund, A. et al., "Group-Contribution Estimation of Activity Coefficients in Nonideal Liquid Mixtures," *AIChE J.* 21:1086, 1975) are rather inadequate due to missing functional groups or collapse of functional group additivity rule with large, complex molecules.

Recently Chen and Song (Chen, C.-C. and Y. Song, "Solubility Modeling with NonRandom Two-Liquid Segment Activity Coefficient Model," *Industrial and Engineering Chemistry Research*, 43:8354, 2004a) and the related U.S. patent application Ser. No. 10/785,925, proposed a NonRandom Two-Liquid segment activity coefficient (NRTL-SAC) model for fast, qualitative correlation and estimation of solubility of organic nonelectrolytes in common solvents and solvent mixtures. Conceptually, the approach suggests that one could account for the liquid phase nonideality of mixtures of small solvent molecules and complex chemical molecules in terms of pre-defined conceptual segments with pre-determined binary interaction characteristics. Examples of the conceptual segments are hydrophobic segment, polar segment, and hydrophilic segment. The numbers of conceptual segments for each molecule, solvent or solute, reflect the characteristic surface interaction area and nature of the surface interactions. While loosely correlated with molecular structure, they are identified from true behavior of the molecules in solution, i.e., available experimental phase equilibrium data. The molecular make-up in terms of numbers of conceptual segments, i.e. hydrophobicity $X$, polarity types $Y-$ and $Y+$, and hydrophilicity $Z$, constitutes the molecular parameters for the solvent and solute molecules. Given the molecular parameters for solvent and solute molecules, the model offers a thermodynamically consistent expression for estimation of phase behavior, including solubilities, for organic nonelectrolytes in chemical process design.

SUMMARY OF THE INVENTION

The recently developed NRTL-SAC model (parent patent application) proves to be an effective tool for the correlation and prediction of nonelectrolyte molecule solubility in single and mixed solvent systems. The present invention extends the NRTL-SAC model to salts as much of chemical synthesis and medicinal therapy are derived from or administered as salts. The present invention provides a simple and practical qualitative ionic activity coefficient model to support the early stage solvent selection of manufacturing process development for salts and help define the impact of polymorphism from a theoretical perspective.

In some embodiments, the present invention features a method of modeling at least one physical property of a mixture of at least one electrolyte dissolved in one or more solvents. In one embodiment, the method comprises computer implemented steps of determining a conceptual electrolyte segment for the electrolyte, using the determined conceptual electrolyte segment, computing at least one physical property of the mixture, and providing an analysis of the computed physical property. The step of determining a conceptual electrolyte segment includes defining a segment number. The analysis forms a model of at least one physical property of the mixture.

The electrolyte can be organic or inorganic, symmetrical or unsymmetrical, or univalent or multivalent. The electrolyte can be a pharmaceutical compound, a nonpolymeric compound, a polymer or an oligomer. The electrolyte may include two or more ionic species.

In one embodiment, the conceptual electrolyte segment includes a cationic segment and an anionic segment. Both segments are of unity charge. The step of computing at least one physical property includes calculating an ionic activity coefficient of the electrolyte.

In further embodiment, the present invention includes a method of modeling at least one physical property of a mixture of at least one electrolyte dissolved in one or more solvents. The method comprises the computer implemented steps of determining a combination of conceptual segments including at least one conceptual electrolyte segment for the electrolyte, using one or more of the conceptual electrolyte segments, computing at least one physical property of the mixture, and providing an analysis of the computed physical property. For each conceptual segment the step of determining a combination of conceptual segments includes defining a segment number. The analysis forms a model of at least one physical property of the mixture. The conceptual segments can include a polar segment, a hydrophilic segment, a hydrophobic segment and an electrolyte segment.

In another embodiment, this invention features a method of modeling at least one physical property of a mixture of at least one chemical compound dissolved in one or more solvents. The method comprises the computer implemented steps of: determining a conceptual electrolyte segment for the chemical component, using the determined conceptual electrolyte segment, computing at least one physical property of the mixture, and providing an analysis of the computed physical property. The step of determining a conceptual electrolyte segment includes defining a segment number. The analysis forms a model of at least one physical property of the mixture.

In further embodiments, the present invention provides a computer program product or computer system carrying out the above invention methods.

In one embodiment, the computer system comprises a user input means for obtaining or defining chemical data from a user, a digital processor coupled to receive the chemical data input from the input means, and an output means coupled to the digital processor. The output means provides to the user the formed model of the physical property of a mixture. The digital processor executes a modeling system in working memory. The modeling system: (i) uses the chemical data to determine a conceptual electrolyte segment for a subject electrolyte, including defining a segment number; (ii) uses the determined conceptual electrolyte segment to compute at least one physical property of a mixture formed of the subject electrolyte; and (iii) provides an analysis of the computed physical property. The analysis forms a model of at least one physical property of the mixture.

In some embodiments, the present invention features a chemical and/or pharmaceutical compound manufactured by a process that employs the above modeling methods.

In some embodiments, the present invention features a chemical or pharmaceutical compound comprising at least one electrolyte. The electrolyte is selected by a model of the modeling methods and systems above. The model determines a conceptual electrolyte segment of the electrolyte and computes physical properties of the electrolyte.

Accordingly, the present invention provides for the fast, practical modeling of physical properties or behaviors of mixtures of at least one electrolyte dissolved in one or more solvents, even when there is little or no experimental data to which the behavior of the mixture can be correlated. The formed models offer improved accuracy over most or all prior modeling methods. For example, this invention offers a simple and practical tool for practitioners to estimate solubility of various components of a mixture (e.g., a mixture including a chemical compound), even when there is little or no phase equilibrium data available for the mixture.

This invention provides for modeling of mixtures having significant electrolyte interactions, hydrophobic interactions, polar interactions, and/or hydrophilic interactions. This invention eliminates the need to characterize mixture constituents with sets of pre-defined functional groups and provides for the modeling of mixtures comprising large, complex electrolytes for which a functional group additivity rule becomes invalid and/or for which there are a number of undefined functional groups.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
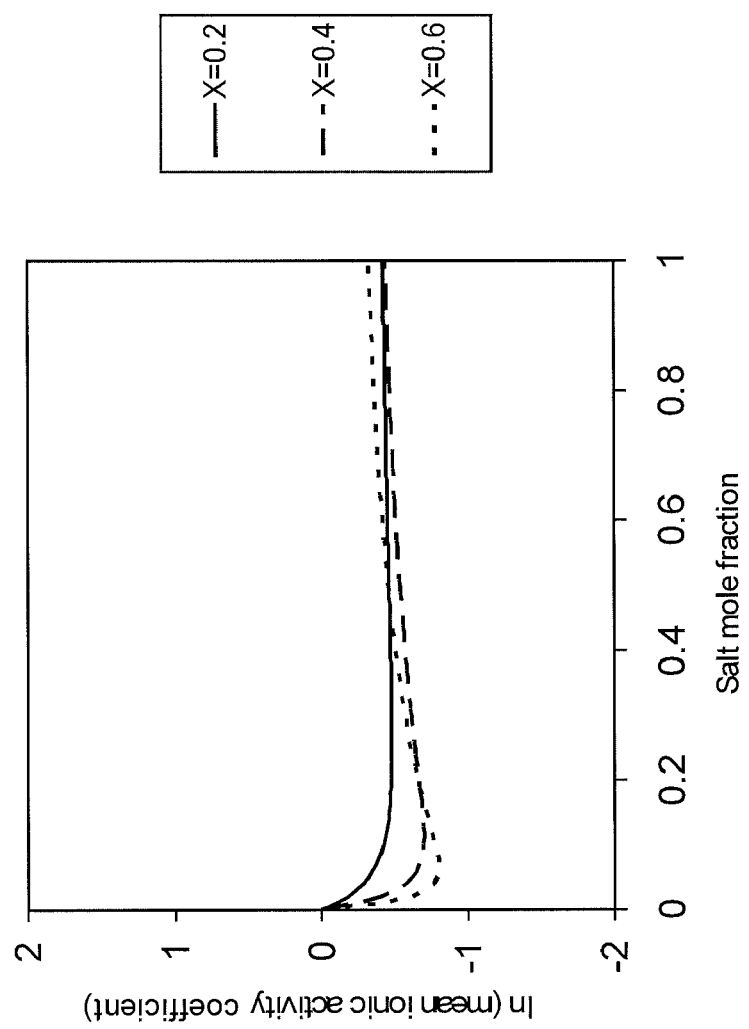
FIG. 1 is a graph illustrating the effect of hydrophobicity parameter X on natural logarithm of mean ionic activity coefficient of aqueous electrolytes with E=1.
Figure 2:
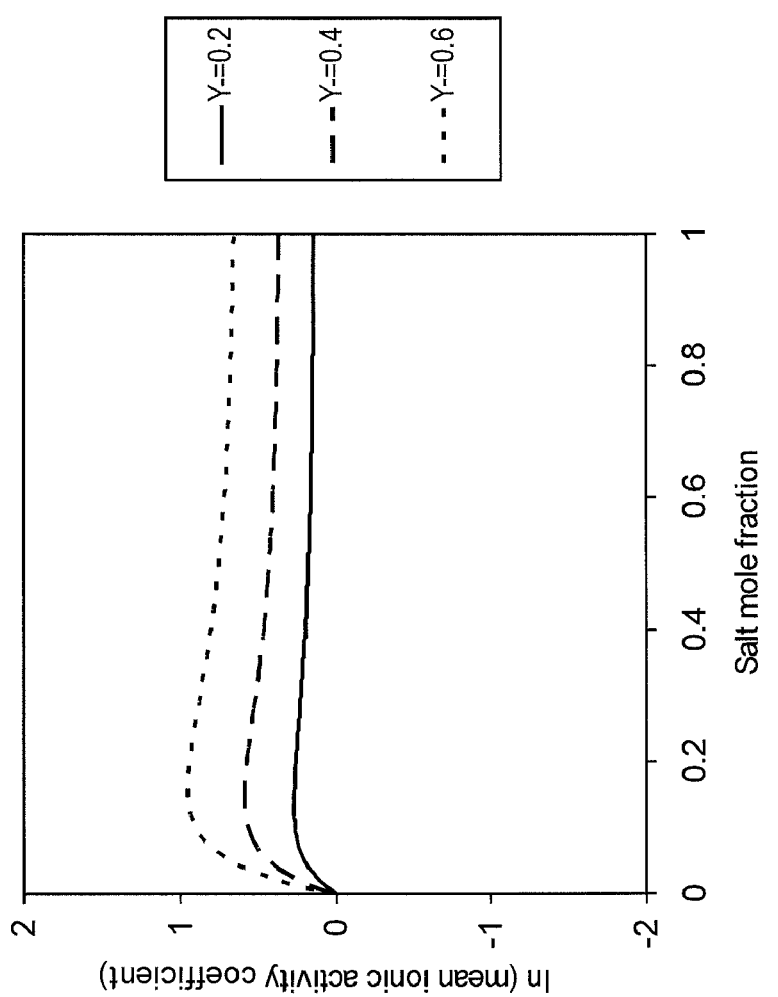
FIG. 2 is a graph illustrating the effect of polarity parameter Y− on natural logarithm of mean ionic activity coefficient of aqueous electrolytes with E=1.
Figure 3:
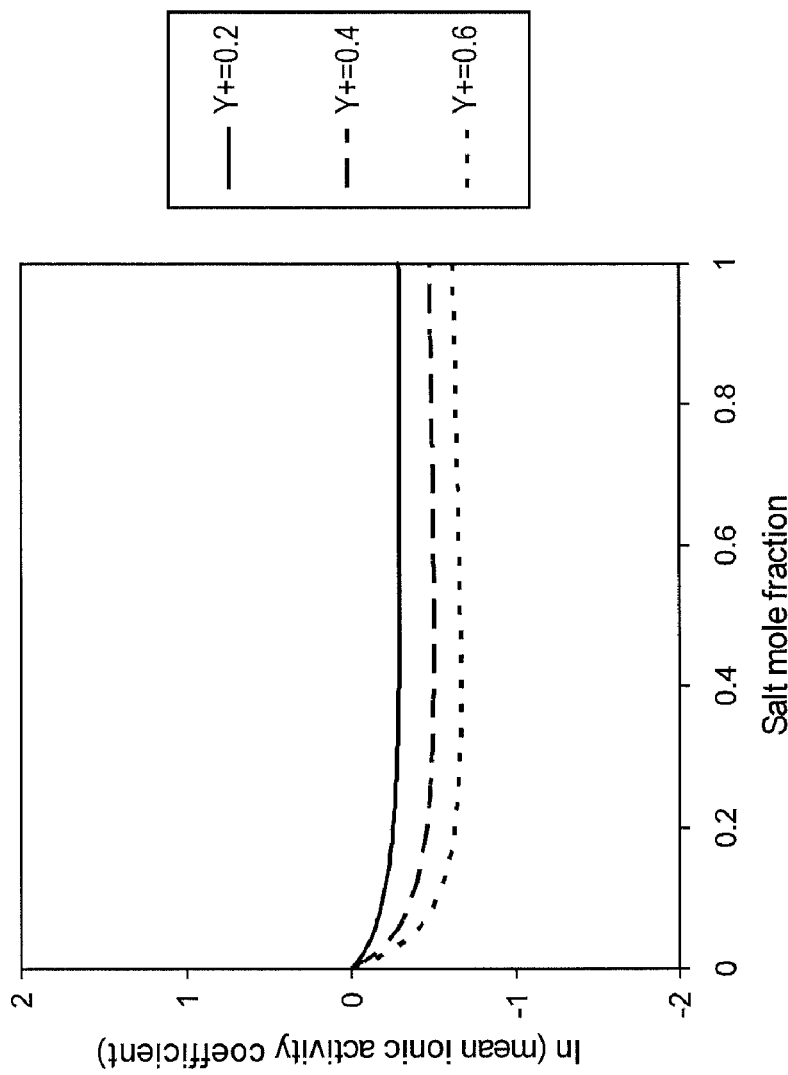
FIG. 3 is a graph illustrating the effect of polarity parameter Y+ on natural logarithm of mean ionic activity coefficient of aqueous electrolytes with E=1.
Figure 4:
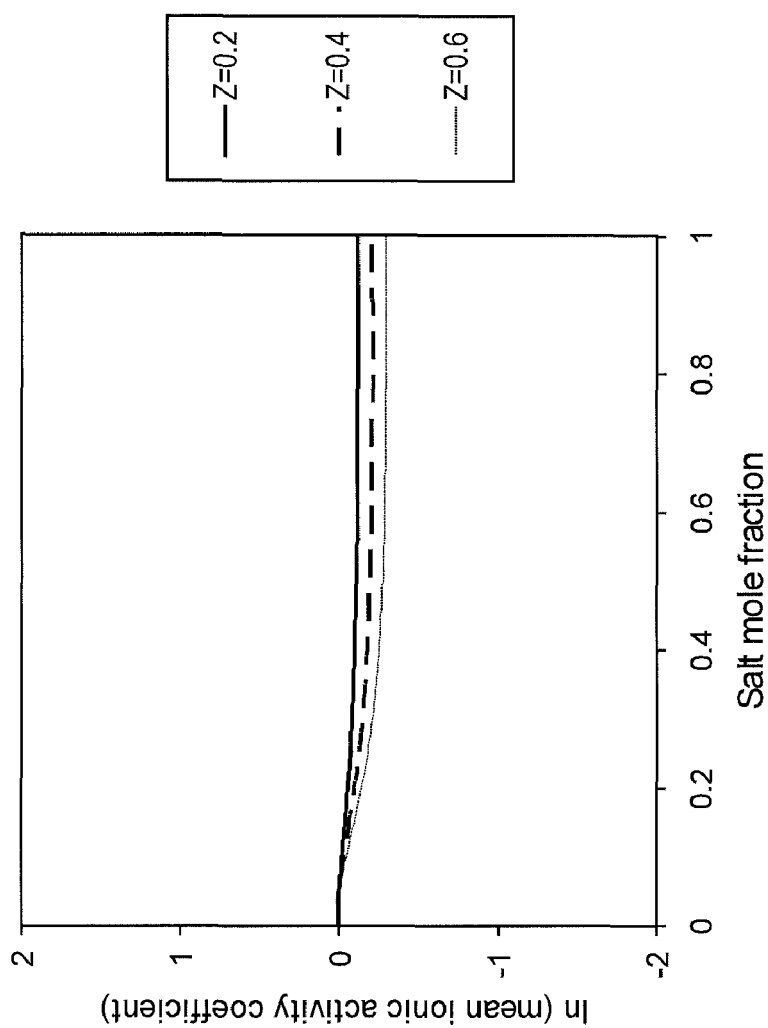
FIG. 4 is a graph illustrating the effect of hydrophilicity parameter Z on natural logarithm of mean ionic activity coefficient of aqueous electrolytes with E=1.
Figure 5:
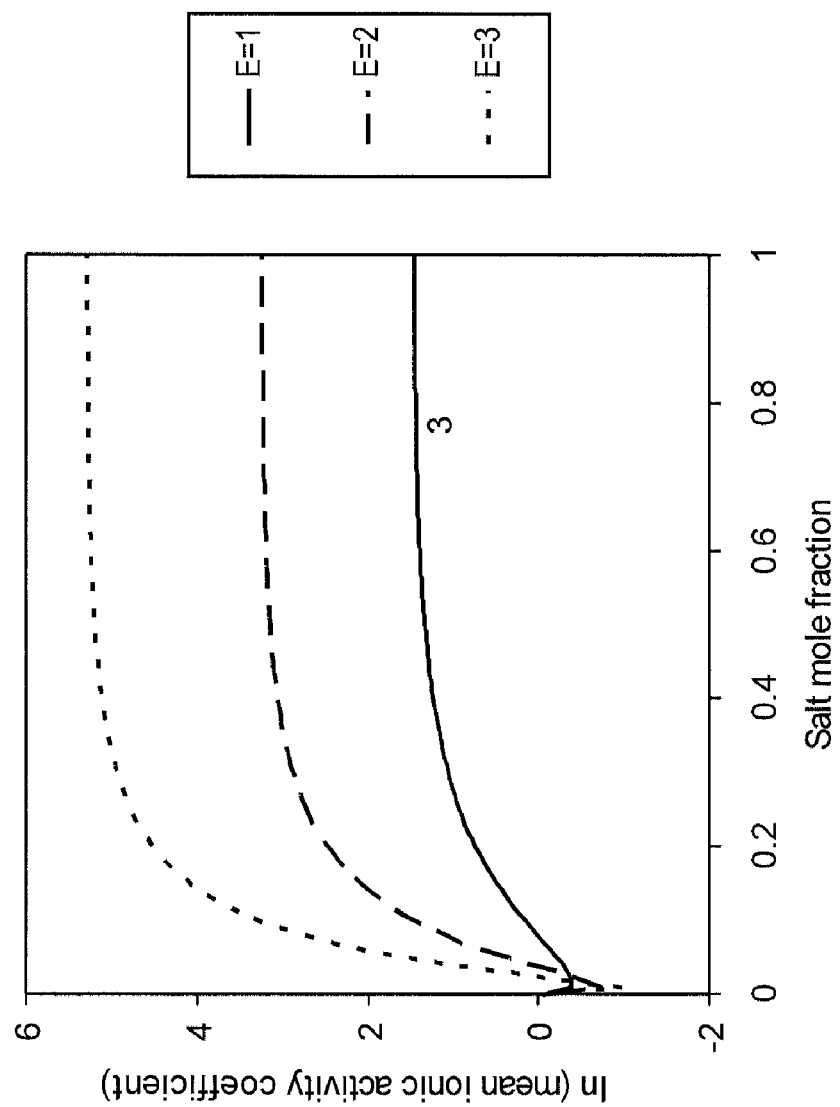
FIG. 5 is a graph illustrating the effect of electrolyte parameter E on natural logarithm of mean ionic activity coefficient of aqueous electrolytes.

Electrolytes are substances which exist as free ions or dissociate into free ions when dissolved to produce an electrically conductive medium. Electrolytes generally exist as salts. Salts have a vast array of chemical and medicinal applications. Predicting the phase behaviors of the electrolytes/salts can assist chemists in the design and in the synthesis of a molecule. For example, it is estimated that half of all drug molecules used in medicinal therapy are administered as salts (Stahl, P. H. and C. F. Wermuth, (Eds.), *Handbook of Pharmaceutical Salts: Properties, Selection and Use*, Verlag Helvetica Chimica Acta, Zürich, Switzerland (2002)). The NRTL-SAC model (parent application/invention) for organic nonelectrolytes is extended to account for the liquid phase nonideality due to presence of ionic charges in organic electrolytes. Applicants have developed a simple and practical qualitative ionic activity coefficient model to aid in designing the chemical process for salts. The extension represents a major advance to the scope of the NRTL-SAC thermodynamic framework. In the absence of organic moiety, organic electrolytes become inorganic electrolytes. In the absence of ionized moiety, organic electrolytes become organic nonelectrolytes. The electrolyte extension of NRTL-SAC model (present invention eNRTL-SAC) provides a consistent and comprehensive thermodynamic framework for systems involving all types of electrolytes and nonelectrolytes. In other words, the NRTL-SAC model of the parent invention/application becomes a limiting case for the present invention eNRTL-SAC model.

NRTL Segment Activity Coefficient Model

The NRTL-SAC activity coefficient model for component I is composed of the combinatorial term $\gamma_I^C$ and the residual term $\gamma_I^R$:

$$\ln \gamma_I = \ln \gamma_I^C + \ln \gamma_I^R \quad (1)$$

Here the combinatorial term $\gamma_I^C$ is calculated from the Flory-Huggins equation for the combinatorial entropy of mixing. The residual term $\gamma_I^R$ is calculated from the local composition (lc) interaction contribution $\gamma_I^{lc}$ of Polymer NRTL (Chen, C.-C., "A Segment-Based Local Composition Model for the Gibbs Energy of Polymer Solutions," *Fluid Phase Equilibria*, 83:301, 1993) (herein "Chen 1993"). The Polymer NRTL equation incorporates the segment interaction concept and computes activity coefficient for component I in a solution by summing up contributions to activity coefficient from all segments that make up component I. The equation is given as follows:

$$\ln \gamma_I^R = \ln \gamma_I^{lc} = \sum_m r_{m,I} [\ln \Gamma_m^{lc} - \ln \Gamma_m^{lc,I}] \quad (2)$$

with $$\ln \Gamma_m^{lc} = \frac{\sum_j x_j G_{jm} \tau_{jm}}{\sum_k x_k G_{km}} + \sum_{m'} \frac{x_{m'} G_{mm'}}{\sum_k x_k G_{km'}} \left( \tau_{mm'} - \frac{\sum_j x_j G_{jm'} \tau_{jm'}}{\sum_k x_k G_{km'}} \right) \quad (3)$$

$$\ln \Gamma_m^{lc,I} = \frac{\sum_j x_{j,I} G_{jm} \tau_{jm}}{\sum_k x_{k,I} G_{km}} + \sum_{m'} \frac{x_{m',I} G_{mm'}}{\sum_k x_{k,I} G_{km'}} \left( \tau_{mm'} - \frac{\sum_j x_{j,I} G_{jm'} \tau_{jm'}}{\sum_k x_{k,I} G_{km'}} \right) \quad (4)$$

$$x_j = \frac{\sum_I x_I r_{j,I}}{\sum_I \sum_i x_I r_{i,I}} \quad x_{j,I} = \frac{r_{j,I}}{\sum_i r_{i,I}} \quad (5)$$

where I is the component index, i, j, k, m, m' are the segment species index, $x_I$ is the mole fraction of component I, $x_j$ is the segment-based mole fraction of segment species j, $r_{m,I}$ is the number of segment species m contained only in component I, $\Gamma_m^{lc}$ is the activity coefficient of segment species m, and $\Gamma_m^{lc,I}$ is the activity coefficient of segment species m contained only in component I. G and $\tau$ in Eqs. 3 and 4 are local binary quantities related to each other by the NRTL non-random factor parameter $\alpha$:

$$G = \exp(-\alpha \tau). \quad (6)$$

Four pre-defined conceptual segments were suggested by Chen and Song (2004 above and in parent patent application): one hydrophobic (x), two polar (y− and y+), and one hydrophilic (z). The model molecular parameters, i.e., hydrophobicity X, polarity types Y− and Y+, and hydrophilicity Z, correspond to $r_{m,I}$ (m=x, y−, y+, z), numbers of various conceptual segments in component I.

In the notation used throughout this disclosure, subscript I (upper case) refers to components while subscript i (lower case) refers to segments.

eNRTL Segment Activity Coefficient Model

The extension of NRTL-SAC model for electrolytes is based on the generalized eNRTL model as summarized by Chen and Song (Chen, C.-C. and Y. Song, "Generalized Electrolyte NRTL Model for Mixed-Solvent Electrolyte Systems," *AIChE J.*, 50:1928, 2004b herein incorporated by reference) (herein "Chen, 2004b"). Here Applicants briefly present the generalized eNRTL model followed by details of the extended NRTL-SAC model of the present invention.

The generalized eNRTL model is applied to correlate mean ionic activity coefficient of mixed-solvent electrolyte systems. The segment interaction concept provides the framework to explicitly account for the attractive interaction of ions with the hydrophilic segments of organic solvents and the repulsive interaction of ions with the hydrophobic segments of organic solvents. In the generalized eNRTL model, any component, electrolyte or solvent, can be defined as an oligomer consisting of various segment species. For instance, an organic electrolyte species can be defined as an oligomer consisting of cationic segment, anionic segment and molecular segment. An organic solvent can be also defined as an oligomer consisting of multiple molecular segments of different nature. Accordingly, with the conventional activity coefficient accounting for the local interaction (Chen, 1993) and the long-range interaction, the model that uses the unsymmetric Pitzer-Debye-Hückel (PDH) formula (Pitzer, K. S., "Electrolytes: From Dilute Solutions to Fused Salts," *J. Am. Chem. Soc.*, 102, 2902 (1980)) (herein "Pitzer, 1980") is calculated as follows:

$$\ln \gamma_I^* = \frac{1}{RT} \left( \frac{\partial G_m^{*ex}}{\partial n_I} \right)_{T,P,n_{J \neq I}} \quad (7)$$

$$= \frac{1}{RT} \left( \frac{\partial G_m^{*ex,lc}}{\partial n_I} \right)_{T,P,n_{J \neq I}} + \frac{1}{RT} \left( \frac{\partial G_m^{*ex,PDH}}{\partial n_I} \right)_{T,P,n_{J \neq I}}$$

Or $$\ln \gamma_I^* = \ln \gamma_I^{*,lc} + \ln \gamma_I^{*,PDH} \quad (8)$$

where I is the component index, "*" denotes the unsymmetric convention, $\gamma_I$ is the activity coefficient of the component I in the mixture; R is the gas constant; T is the temperature; P is the pressure; and $n_I$ is the mole number of the component I in the mixture. The unsymmetric PDH formula, $G^{*ex,PDH}_m$, is obtained by normalization to mole fractions of unity for solvents and zero for electrolytes (Pitzer, K. S., "Thermodynamics of Electrolytes. I: Theoretical and General Equations," *J. Phys. Chem.*, 77, 268 (1973)). The local interaction NRTL model, $G^{*ex,lc}_m$, is developed as a symmetric model (Chen, C.-C., "A Segment-Based Local Composition Model for the Gibbs Energy of Polymer Solutions," *Fluid Phase Equilib.*, 83, 301 (1993); and Chen, C.-C., C. P. Bokis, and P. M. Mathias, "A Segment-Based Excess Gibbs Energy Model for Aqueous Organic Electrolyte Systems," *AIChE J.*, 47, 2593 (2001)), based on the symmetrical reference state so that the derived activity coefficient, is $\gamma_I^{lc}=1$ as $x_I \rightarrow 1$ for any component (species). The model is then normalized by the unsymmetric reference state (that is, the infinite-dilution activity coefficient in an aqueous or mixed-solvent solution) to obtain the unsymmetric model, $G_m^{*ex,lc}$. Accordingly, the unsymmetric convention activity coefficient is calculated as follows:

$$\ln \gamma_I^{*lc} = \ln \gamma_I^{lc} - \ln \gamma_I^{\infty lc}, \qquad (9)$$

$$\ln \gamma_I^c = \frac{1}{RT}\left(\frac{\partial G_m^{ex,lc}}{\partial n_I}\right)_{T,P,n_{J \neq I}}, \qquad (10)$$

where $\gamma_I^\infty$ is the infinite-dilution activity coefficient of the ionic component I in an aqueous or mixed-solvent solution as calculated by Equation 10. A more detailed description on the generalized electrolyte-NRTL model is depicted in Chen, 2004b.

This generalized segment interaction concept is advantageous when one must exactly account for the different interaction characteristics that may be attributed to different molecules, solvents or solutes. The ability to exactly account for such different segment-segment interactions between different species in a system is shown to be key for quantitative correlation of mean ionic activity coefficients in mixed-solvent electrolyte systems. In the generalized eNRTL model, however, it is necessary to account for an electrolyte segment for each and every species separately. Therefore, in a system that involves multiple components, there could be tens of different segments to consider and hundreds of segment-segment interactions to account for, and the computation for activity coefficients becomes much more complicated.

Derived from and improved upon the generalized eNRTL model, the electrolyte extension of NRTL model of the present invention provides one conceptual electrolyte segment. A "conceptual electrolyte segment" herein is one predefined electrolyte segment that characterizes the prominent interaction mechanisms between molecules in the liquid phase, that account for the liquid phase nonideality. This pre-defined electrolyte segment is used as a reference against which all electrolyte segments are measured in terms of their liquid phase interaction characteristics. Unlike the generalized eNRTL model, which has no such "conceptual electrolyte segment" as a reference point, surface interaction characteristics of electrolyte segments of the present invention are normalized against the "conceptual electrolyte segment" (in a preferred embodiment, one with interaction characteristics of NaCl) and mathematically expressed as an equivalent number of the reference one. Having a point of reference for the calculation of the electrolyte segment provides a unified and consistent description of liquid phase nonideality of all electrolyte segments and a more intuitive and powerful predictive tool in modeling physical properties including solubility. Together with the numbers of "conceptual" hydrophobic segment, hydrophilic segment and polar segment, the number of "conceptual electrolyte segment" reflects the nature of the surface interactions and their characteristic surface interaction areas that determine their phase behavior.

Electrolytes dissociate to ionic species in solutions. For "strong" electrolytes, the dissociation is "completely" to ionic species. For "weak" electrolytes, the dissociation is partially to ionic species while undissociated electrolytes, similar to nonelectrolytes, remain as neutral molecular species. Complexation of ionic species with solvent molecules or other ionic species may also occur. An implication of the electrolyte solution chemistry is that the extended model should provide a thermodynamically consistent framework to compute activity coefficients for both molecular species and ionic species.

In the simplest case of a strong electrolyte CA, one may use the following chemical reaction to describe the complete dissociation of the electrolyte:

$$CA \rightarrow \upsilon_C C^{z_C} + \upsilon_A A^{z_A} \qquad (11)$$

with

$$\upsilon_C Z_C = \upsilon_A Z_A \qquad (12)$$

where $\upsilon_C$ is the cationic stoichiometric coefficient, $\upsilon_A$ is the anionic stoichiometric coefficient, $Z_C$ is the absolute charge number for cation C, and $Z_A$ is the absolute charge number for anion A.

In applying the segment contribution concept to electrolytes, Applicants introduce a new conceptual electrolyte segment e. This conceptual segment e would completely dissociate to a cationic segment (c) and an anionic segment (a), both of unity charge. Applicants then follow the like-ion repulsion and the electroneutrality constraints imposed by the generalized eNRTL model to derive the activity coefficient equations for ionic segments c and a. All electrolytes, organic or inorganic, symmetric or unsymmetric, univalent or multivalent, are to be represented with this conceptual uni-univalent electrolyte segment e together with previously defined hydrophobic segment, x, polar segments, y– and y+, and hydrophilic segment, z. Due to the fact that Applicants introduce only one (a universally useable one) conceptual electrolyte segment e, the resulting eNRTL-SAC model of the present invention is much simpler than the generalized eNRTL model proposed earlier.

In some embodiments, this invention includes methods and apparatus/systems of modeling at least one physical property of a mixture of at least one electrolyte dissolved in one or more solvents. Preferably, the method, apparatus and system comprise the computer implemented steps of: (a) determining a conceptual electrolyte segment for the electrolyte, including defining a segment number; (b) using the determined conceptual electrolyte segment, computing at least one physical property of the mixture; and (c) providing an analysis of the computed physical property. The analysis forms a model of the at least one physical property of the mixture.

The invention method, apparatus/system models mixtures of one or more electrolytes that are organic or inorganic, symmetrical or unsymmetrical, or univalent or multivalent. The electrolyte may be a chemical compound, a pharmaceutical compound, a nonpolymeric compound, a polymer, an oligomer, an inorganic compound and an organic compound. The electrolyte may include two or more ionic species.

As used herein, a "pharmaceutical compound" can include drugs, therapeutic agents, salts or a precursor thereof (i.e., a compound used as an ingredient in a pharmaceutical compound production process) and all manner of compounds residing within an organism or system, such as nutrients, metabolites, endogenous hormones, toxins, and the likes. In some embodiments, the chemical compound has a weight greater than about 900 daltons, at least one molecule having a molecular weight in the range of between about 100 daltons and about 900 daltons, and/or at least one molecule having a molecular weight in the range of between about 200 daltons and about 600 daltons.

In accordance with one aspect of the present invention, at least one conceptual segment (e.g., at least 1, 2, 3, 4, or more than 4 conceptual segments) is determined or defined for each of the chemical species of a subject mixture. The conceptual segments are molecular descriptors of the various molecular species in the mixture. An identity and an equivalent number are determined for each of the conceptual segments. Examples of identities for conceptual segments include a hydrophobic segment, a polar segment, a hydrophilic segment, an electrolyte segment, and the like. Experimental phase equilibrium data can be used to determine the equivalent number of the conceptual segment(s).

The determined conceptual segments are used to compute at least one physical property of the mixture, and an analysis of the computed physical property is provided to form a model of at least one physical property of the mixture. The present invention enables a wide variety of physical properties to be modeled. Examples of physical properties include an activity coefficient, vapor pressure, solubility (e.g., the equilibrium concentration of one or more chemical species in one or more phases of the mixture), boiling point, freezing point, octanol/water partition coefficient, lipophilicity of the electrolyte and other physical properties that are measured or determined for use in the chemical processes.

The models of the physical property or properties of the mixture are produced by determining the interaction characteristics of the conceptual segments. In some embodiments, the segment-segment interaction characteristics of the conceptual segments are represented by their corresponding binary eNRTL parameters. Given the eNRTL parameters for the conceptual segments and the molecular descriptors for the molecules, the eNRTL-SAC model computes activity coefficients for the segments and then for the various electrolytes in the mixture. In other words, the physical properties or behavior of the mixture will be accounted for based on the segment compositions of the electrolytes and their mutual interactions. In further embodiments, the step of computing at least one physical property includes calculating an activity coefficient of the electrolyte.

For example, the solubility of an electrolyte is described well by the expression:

$$K_{sp}(T) = \prod_C x_C^{v_C,SAT} \gamma_C^{*v_C,SAT} \prod_A x_A^{v_A,SAT} \gamma_A^{*v_A,SAT} \prod_M x_M^{SAT} \gamma_M^{SAT}, \quad (13)$$

where $K_{sp}$ is the solubility product constant for the electrolyte, T is the temperature of the mixture, $x_C^{v_CSAT}$ is the mole fraction of a cation derived from the electrolyte at saturation point of the electrolyte, $x_A^{v_ASAT}$ is the mole fraction of an anion derived from the electrolyte at saturation point of the electrolyte, $x_M^{v_MSAT}$ is the mole fraction of a neutral molecule derived from the electrolyte at saturation point of the electrolyte, $\gamma^*{}_C^{v_C,SAT}$ is the activity coefficient of a cation derived from the electrolyte at the saturation concentration, $\gamma^*{}_A^{v_A,SAT}$ is the activity coefficient of an anion derived from the electrolyte at the saturation concentration, $\gamma^*{}_M^{v_M,SAT}$ is the activity coefficient of a neutral molecule derived from the electrolyte at the saturation concentration, C is the cation, A is the anion, M is solvent or solute molecule, T is the temperature of the mixture, $\gamma^*$ is the unsymmetric activity coefficient of a species in solution, SAT is saturation concentration, $\upsilon_C$ is the cationic stoichiometric coefficient, $\upsilon_A$ is the anionic stoichiometric coefficient, and $\upsilon_m$ is the neutral stoichiometric coefficient.

A major consideration in the extension of NRTL-SAC for electrolytes is the treatment of reference state for activity coefficient calculations. While the conventional reference state for nonelectrolyte systems is the pure liquid component, the conventional reference state for electrolytes in solution is the infinite-dilution aqueous solution and the corresponding activity coefficient is "unsymmetric."

Following the generalized eNRTL model, the logarithm of unsymmetric activity coefficient of an ionic species, $\ln \gamma^*{}_I$, is the sum of three terms: the local composition term, $\ln \gamma^*{}_I^{lc}$, the Pitzer-Debye-Hückel term, $\ln \gamma^*{}_I^{PDH}$, and the Flory-Huggins term, $\ln \gamma^*{}_I^{FH}$.

$$\ln \gamma^*{}_I = \ln \gamma^*{}_I^{lc} + \ln \gamma^*{}_I^{PDH} + \ln \gamma^*{}_I^{FH} \quad (14)$$

Eq. 14 applies to aqueous electrolyte systems where water is a sole solvent within the solution. For mixed-solvent solutions, the Born term, $\Delta \ln \gamma_I^{Born}$, is used to correct the change of the infinite dilution reference state from the mixed-solvent composition to the aqueous solution for the Pitzer-Debye-Hückel term:

$$\ln \gamma^*{}_I = \ln \gamma^*{}_I^{lc} + \ln \gamma^*{}_I^{PDH} + \ln \gamma^*{}_I^{FH} + \Delta \ln \gamma_I^{Born} \quad (15)$$

Since Applicants adopt the aqueous phase infinite dilution reference state for $\gamma^*{}_I$, the Born term correction is required for non-aqueous systems.

With the introduction of the conceptual electrolyte segment e and the corresponding conceptual ionic segments c and a, one can rewrite Eq. 15 in terms of contributions from all conceptual segments:

$$\begin{aligned}\ln\gamma_I^* &= \ln\gamma_I^{*lc} + \ln\gamma_I^{*PDH} + \ln\gamma_I^{*FH} + \Delta\ln\gamma_I^{Born} \\ &= \sum_m r_{m,I}(\ln\Gamma_m^{*lc} + \ln\Gamma_m^{*PDH}) + \\ &\quad r_{c,I}(\ln\Gamma_c^{*lc} + \ln\Gamma_c^{*PDH} + \Delta\ln\Gamma_c^{Born}) + \\ &\quad r_{a,I}(\ln\Gamma_a^{*lc} + \ln\Gamma_a^{*PDH} + \Delta\ln\Gamma_a^{Born}) + \ln\gamma_I^{*FH}\end{aligned} \quad (16)$$

where r is the segment number, m is the conceptual molecular segment index (i.e., m=x, y−, y+, z), c and a are cationic and anionic segments, respectively, resulting from the dissociation of the conceptual electrolyte segment e. Also notice that in Eq. 16, unlike the local composition term and the long range ion-ion interaction terms, the Flory-Huggins term remains as the component-based contribution.

For systems of single electrolyte CA with a segment number $r_e$, $r_c$ and $r_a$ must satisfy electroneutrality and they can be computed from $r_e$, $Z_C$, and $Z_A$.

$$r_{c,C} = r_{e,CA} Z_C \quad (17)$$

$$r_{a,A} = r_{e,CA} Z_A \quad (18)$$

For systems of multiple electrolytes, the mixing rule is needed to compute segment number $r_c$ and $r_a$ for each cation C and anion A.

$$r_{c,C} = \sum_A r_{e,CA} Z_C \left( x_A Z_A \Big/ \sum_{A'} x_{A'} Z_{A'} \right) \quad (19)$$

$$r_{a,C} = \sum_C r_{e,CA} Z_A \left( x_C Z_C \Big/ \sum_{C'} x_{C'} Z_{C'} \right) \quad (20)$$

$r_{e,CA}$, the number of conceptual electrolyte segment e in electrolyte CA, becomes the new model parameter for electrolytes. For the sake of brevity, Applicants call $r_{e,CA}$ parameter E, the electrolyte segment number.

Local Composition Interaction Contribution

To derive the expression for the local composition interaction contribution, Applicants simplify the generalized excess Gibbs energy expression of the prior Chen and Song model (Chen, 2004b) for systems with multiple molecular segments m and single electrolyte segment e. The single electrolyte segment e is then decomposed into a cationic segment c and an anionic segment a:

$$\frac{G^{ex,lc}}{nRT} = \sum_I \left[ \sum_m r_{m,I} x_I \left( \frac{\sum_j x_j G_{jm} \tau_{jm}}{\sum_k x_k G_{km}} \right) + r_{c,I} x_I \left( \frac{\sum_j x_j G_{jc,ac} \tau_{jc,ac}}{\sum_k x_k G_{kc,ac}} \right) + r_{a,I} x_I \left( \frac{\sum_j x_j G_{ja,ca} \tau_{ja,ca}}{\sum_k x_k G_{ka,ca}} \right) \right] \quad (21)$$

with $$x_j = \frac{\sum_I x_I r_{j,I}}{\sum_I \sum_i x_I r_{i,I}} \quad i,j = m, c, a \quad (22)$$

where $G^{ex,lc}$ is the excess Gibbs energy from local composition interactions, n is the total mole number, R is the gas constant and T is the temperature.

To derive the segment activity coefficient, one can rewrite Eq. 21 as follows:

$$\frac{G^{ex,lc}}{n_S RT} = \sum_m x_m \left( \frac{\sum_j x_j G_{jm} \tau_{jm}}{\sum_k x_k G_{km}} \right) + x_c \left( \frac{\sum_j x_j G_{jc,ac} \tau_{jc,ac}}{\sum_k x_k G_{kc,ac}} \right) + x_a \left( \frac{\sum_j x_j G_{ja,ca} \tau_{ja,ca}}{\sum_k x_k G_{ka,ca}} \right) \quad (23)$$

where $n_S$ is the total number of all segments. Accordingly, the segment activity coefficient can be calculated as follows:

$$\ln \Gamma_j^{lc} = \frac{1}{RT} \left( \frac{\partial G^{ex,lc}}{\partial n_j} \right)_{T,P,n_{i \neq j}} \quad i,j = m, c, a \quad (24)$$

Specifically, the activity coefficients from Eq. 24 for molecular segments, cationic segment, and anionic segment can be carried out as follows:

$$\ln \Gamma_m^{lc} = \frac{\sum_j x_j G_{jm} \tau_{jm}}{\sum_k x_k G_{km}} + \sum_{m'} \frac{x_{m'} G_{mm'}}{\sum_k x_k G_{km'}} \left( \tau_{mm'} - \frac{\sum_j x_j G_{jm'} \tau_{jm'}}{\sum_k x_k G_{km'}} \right) + \quad (25)$$

$$\frac{x_c G_{mc,ac}}{\sum_k x_k G_{kc,ac}} \left( \tau_{mc,ac} - \frac{\sum_j x_j G_{jc,ac} \tau_{jc,ac}}{\sum_k x_k G_{kc,ac}} \right) +$$

$$\frac{x_a G_{ma,ca}}{\sum_k x_k G_{ka,ca}} \left( \tau_{ma,ca} - \frac{\sum_j x_j G_{ja,ca} \tau_{ja,ca}}{\sum_k x_k G_{ka,ca}} \right)$$

$$\ln \Gamma_c^{lc} = \sum_m \frac{x_m G_{cm}}{\sum_k x_k G_{km}} \left( \tau_{cm} - \frac{\sum_j x_j G_{jm} \tau_{jm}}{\sum_k x_k G_{km}} \right) + \quad (26)$$

$$\frac{\sum_j x_j G_{jc,ac} \tau_{jc,ac}}{\sum_k x_k G_{kc,ac}} - \frac{x_a}{\sum_k x_k G_{ka,ca}} \left( \frac{\sum_j x_j G_{ja,ca} \tau_{ja,ca}}{\sum_k x_k G_{ka,ca}} \right)$$

$$\ln \Gamma_a^{lc} = \sum_m \frac{x_m G_{am}}{\sum_k x_k G_{km}} \left( \tau_{am} - \frac{\sum_j x_j G_{jm} \tau_{jm}}{\sum_k x_k G_{km}} \right) + \quad (27)$$

$$\frac{\sum_j x_j G_{ja,ca} \tau_{ja,ca}}{\sum_k x_k G_{ka,ca}} - \frac{x_c}{\sum_k x_k G_{kc,ac}} \left( \frac{\sum_m x_m G_{mc,ac} \tau_{mc,ac}}{\sum_k x_k G_{kc,ac}} \right)$$

The local composition term for the logarithm of activity coefficient of component I is computed as the sum of the individual segment contributions.

$$\ln \gamma_I^{lc} = \sum_i r_{i,I} \ln \Gamma_i^{lc} \quad i = m, c, a \quad (28)$$

$$\sum_m r_{m,I} \ln \Gamma_m^{lc} + r_{c,I} \ln \Gamma_c^{lc} + r_{a,I} \ln \Gamma_a^{lc}$$

However, the activity coefficient by Eq. 28 needs to be further normalized so that $\gamma_I^{lc}=1$ as $x_I \to 1$ for any component; this is the so-called symmetric reference state. The normalization can be done as follows:

$$\ln \gamma_I^{lc} = \sum_i r_{i,I} [\ln \Gamma_i^{lc} - \ln \Gamma_i^{lc,I}] \quad i = m, c, a \quad (29)$$

$$= \sum_m r_{m,I} [\ln \Gamma_m^{lc} - \ln \Gamma_m^{lc,I}] + r_{c,I} [\ln \Gamma_c^{lc} - \ln \Gamma_c^{lc,I}] +$$

$$r_{a,I} [\ln \Gamma_a^{lc} - \ln \Gamma_a^{lc,I}]$$

Here $\Gamma_i^{lc,I}$ is the activity coefficient of the segment i contained in the symmetric reference state of component I; it can be calculated from Eqs. 25-27 by setting $x_I=1$:

$$\ln \Gamma_i^{lc,I} = \ln \Gamma_i^{lc}(x_I=1) \quad i=m,c,a \quad (30)$$

Finally, the unsymmetric convention in Eq. 15 requires us to compute the infinite-dilution activity coefficient, $\gamma_I^{\infty lc}$, for a component:

$$\ln \gamma_I^{*lc} = \ln \gamma_I^{lc} - \ln \gamma_I^{\infty lc} \quad (31)$$

with $$\ln \gamma_I^{\infty lc} = \sum_i r_{i,I}[\ln \Gamma_i^{\infty lc} - \ln \Gamma_i^{lc,I}] \quad i = m, c, a \quad (32)$$

$$= \sum_m r_{m,I}[\ln \Gamma_m^{\infty lc} - \ln \Gamma_m^{lc,I}] + r_{c,I}[\ln \Gamma_c^{\infty lc} - \ln \Gamma_c^{lc,I}] +$$

$$r_{a,I}[\ln \Gamma_a^{\infty lc} - \ln \Gamma_a^{lc,I}]$$

Combining Eqs. 29 and 32, one can obtain:

$$\ln \gamma_I^{*lc} = \ln \gamma_I^{lc} - \ln \gamma_I^{\infty lc} \quad (33)$$

$$= \sum_i r_{i,I}[\ln \Gamma_i^{lc} - \ln \Gamma_i^{\infty lc}] \quad i = m, c, a$$

$$= \sum_m r_{m,I}[\ln \Gamma_m^{lc} - \ln \Gamma_m^{\infty lc}] + r_{c,I}[\ln \Gamma_c^{lc} - \ln \Gamma_c^{\infty lc}] +$$

$$r_{a,I}[\ln \Gamma_a^{lc} - \ln \Gamma_a^{\infty lc}]$$

$$= \sum_m r_{m,I} \ln \Gamma_m^{*lc} + r_{c,I} \ln \Gamma_c^{*lc} + r_{a,I} \ln \Gamma_a^{*lc}$$

with $$\ln \Gamma_m^{*lc} = \ln \Gamma_m^{lc} - \ln \Gamma_m^{\infty lc} \quad (34)$$

$$\ln \Gamma_c^{*lc} = \ln \Gamma_c^{lc} - \ln \Gamma_c^{\infty lc} \quad (35)$$

$$\ln \Gamma_a^{*lc} = \ln \Gamma_a^{lc} - \ln \Gamma_a^{\infty lc} \quad (36)$$

Because Applicants adopt the aqueous phase infinite dilution reference state, the infinite-dilution activity coefficients of conceptual segments can be calculated from Eqs. 25-28 by setting $x_W = 1$:

$$\ln \Gamma_i^{\infty lc} = \ln \Gamma_i^{lc}(x_W=1) \quad i=m,c,a \quad (37)$$

where $x_W$ is the mole fraction of water in the solution.

Long-Range Interaction Contribution from Pitzer-Debye-Hückel (PDH) Model

To account for the long-range ion-ion interactions, the present invention eNRTL-SAC model uses the unsymmetric Pitzer-Debye-Hückel (PDH) formula (Pitzer, 1980) on the segment basis:

$$\frac{G^{*ex,PDH}}{n_S RT} = -\left(\frac{1000}{\overline{M}_S}\right)^{\frac{1}{2}} \left(\frac{4 A_\varphi I_x}{\rho}\right) \ln(1 + \rho I_x^{\frac{1}{2}}) \quad (38)$$

with $$A_\varphi = \frac{1}{3}\left(\frac{2\pi N_A \overline{d}_S}{1000}\right)^{\frac{1}{2}} \left(\frac{Q_e^2}{\overline{\varepsilon}_S k_B T}\right)^{\frac{3}{2}} \quad (39)$$

$$I_x = \frac{1}{2}\sum_i x_i z_i^2 \quad (40)$$

where $A_\varphi$ is the Debye-Hückel parameter, $I_x$ is the ionic strength (segment mole fraction scale), $\overline{M}_S$ is the average molecular weight of the mixed-solvents, $\rho$ is the closest approach parameter, $N_A$ is the Avogadro's number, $\overline{d}_S$ is the average density of the mixed-solvents, $Q_e$ is the electron charge, $\overline{\varepsilon}_S$ is the average dielectric constant of the mixed-solvents, $k_B$ is the Boltzmann constant, and $z_i (z_m=0; z_c=z_a=1)$ is the charge number of segment-based species i.

Applying the PDH model to the conceptual segments, the activity coefficient of segment species i can be derived as follows:

$$\ln \Gamma_i^{*PDH} = \frac{1}{RT}\left(\frac{\partial G^{*ex,PDH}}{\partial n_i}\right)_{T,P,n_{j \ne i}} \quad (41)$$

$$= -\left(\frac{1000}{\overline{M}_S}\right)^{\frac{1}{2}} A_\varphi \left[\left(\frac{2 z_i^2}{\rho}\right)\ln(1 + \rho I_x^{\frac{1}{2}}) + \frac{z_i^2 I_x^{\frac{1}{2}} - 2 I_x^{\frac{3}{2}}}{1 + \rho I_x^{\frac{1}{2}}}\right]$$

$i, j = m, c, a$

The unsymmetric long range term for the logarithm of activity coefficient of component I is the sum of contributions from its various segments:

$$\ln \gamma_I^{*PDH} = \sum_m r_{m,I} \ln \Gamma_m^{*PDH} + r_{c,I} \ln \Gamma_c^{*PDH} + r_{a,I} \ln \Gamma_a^{*PDH} \quad (42)$$

where $$\ln \Gamma_m^{*PDH} = 2\left(\frac{1000}{\overline{M}_S}\right)^{\frac{1}{2}} \frac{A_\varphi I_x^{\frac{3}{2}}}{1 + \rho I_x^{\frac{1}{2}}} \quad (43)$$

$$\ln \Gamma_c^{*PDH} = \ln \Gamma_a^{*PDH} = -\left(\frac{1000}{\overline{M}_S}\right)^{\frac{1}{2}} A_\varphi \left[\left(\frac{2}{\rho}\right)\ln(1 + \rho I_x^{\frac{1}{2}}) + \frac{I_x^{\frac{1}{2}} - 2 I_x^{\frac{3}{2}}}{1 + \rho I_x^{\frac{1}{2}}}\right] \quad (44)$$

With $$A_\varphi = \frac{1}{3}\left(\frac{2\pi N_A \overline{d}_S}{1000}\right)^{\frac{1}{2}} \left(\frac{Q_e^2}{\overline{\varepsilon}_S k_B T}\right)^{\frac{3}{2}} \quad (45)$$

$$I_x = \frac{1}{2}(x_c + x_a) \quad (46)$$

The Debye-Hückel theory is based on the infinite dilution reference state for ionic species in the actual solvent media. For systems with water as the only solvent, the reference state is the infinite dilution aqueous solution. For mixed-solvent systems, the reference state for which the Pitzer-Debye-Hückel formula remains valid is the infinite dilution solution with the corresponding mixed-solvent composition. Consequently, the molecular quantities for the single solvent need to be extended for mixed-solvents; simple composition average mixing rules are adequate to calculate them as follows:

$$\overline{M}_S = \sum_S x_S' M_S \quad (47)$$

$$\frac{1}{\overline{d}_S} = \sum_S \frac{x_S'}{d_S} \quad (48)$$

$$\overline{\varepsilon}_S = \sum_S w_S' \varepsilon_S \quad (49)$$

with $$x_S' = \frac{x_S}{\sum_S x_S} \quad (50)$$

$$w_S' = \frac{M_S x_S}{\sum_S M_S x_S} \quad (51)$$

where S is a solvent component in the mixture, and $M_S$ is the molecular weight of the solvent S. It should be pointed out that Eqs. 47-51 should be used only in Eq. 41 and $\overline{M}_S$, $\overline{d}_S$, and $\overline{\varepsilon}_S$ were already assumed as constants in Eqs. 38 and 39 when deriving Eq. 41 for mixed-solvent systems. Table 1 shows the values of dielectric constant at 298.15 K used in this study for the same sixty-two solvents investigated by Chen and Song (Chen, 2004a and U.S. application Ser. No. 10/785,925) above. These values were compiled from various sources including internet websites and commercial software Aspen Properties v2004.1 (by Aspen Technology, Inc. of Cambridge, Mass., assignee of the present invention).

Born Term Correction to Activity Coefficient

Given that the infinite dilution aqueous solution is chosen as the reference state, one needs to correct the change of the reference state from the mixed-solvent composition to aqueous solution for the Pitzer-Debye-Hüekel term. The Born term (Robinson, R. A. and R. H. Stokes, *Electrolyte Solutions*, $2^{nd}$ ed., Butterworths (1970), Rashin, A. A. and B. Honig, "Reevaluation of the Born Model of Ion Hydration, *J. Phys. Chem.*, 89: 5588 (1985)) on the segment basis is used for this purpose:

$$\frac{\Delta G^{Born}}{n_S RT} = \frac{Q_e^2}{2k_B T}\left(\frac{1}{\varepsilon_S} - \frac{1}{\varepsilon_W}\right)\sum_i \frac{x_i z_i^2}{r_i} 10^{-2} \quad (52)$$

$\Delta G^{Born}$ is the Born term correction to the unsymmetric Pitzer-Debye-Hückel formula, $G^{*ex,PDH}$, $\varepsilon_W$ is the dielectric constant of water, and $r_i$ is the Born radius of segment specie i.

Applying Eq. 52 to all conceptual segments, the corresponding expression for the activity coefficient of segment species i can be derived as follows:

$$\Delta \ln \Gamma_m^{Born} = \frac{1}{RT}\left(\frac{\partial \Delta G^{Born}}{\partial n_m}\right)_{T,P,n_{j\neq m}} = 0 \quad (53)$$

$m = x, y-, y+, z$ $$\Delta \ln \Gamma_i^{Born} = \frac{1}{RT}\left(\frac{\partial \Delta G^{Born}}{\partial n_i}\right)_{T,P,n_{j\neq i}} \quad (54)$$

$$= \frac{Q_e^2}{2k_B T}\left(\frac{1}{\varepsilon_S} - \frac{1}{\varepsilon_W}\right)\frac{z_i^2}{r_i} 10^{-2}$$

$i = c, a$

The Born correction term on the logarithm of activity coefficient of component I is the sum of contributions from its various segments:

$$\Delta \ln \gamma_I^{Born} = r_{c,I}\Delta \ln \Gamma_c^{Born} + r_{a,I}\Delta \ln \Gamma_a^{Born} \quad (55)$$

$$\Delta \ln \Gamma_c^{Born} = \frac{Q_e^2}{2k_B T}\left(\frac{1}{\varepsilon_S} - \frac{1}{\varepsilon_W}\right)\frac{1}{r_c} 10^{-2} \quad (56)$$

$$\Delta \ln \Gamma_a^{Born} = \frac{Q_e^2}{2k_B T}\left(\frac{1}{\varepsilon_S} - \frac{1}{\varepsilon_W}\right)\frac{1}{r_a} 10^{-2} \quad (57)$$

Flory-Huggins Term Correction to Activity Coefficient

Although in most common electrolyte systems, the combinatorial entropy of mixing term is much smaller than the residual term, one may still want to include it in a general model. Applicants follow the Polymer NRTL model (Chen 1993 above) and use the Flory-Huggins term to describe the combinatorial term:

$$\frac{G^{ex,FH}}{nRT} = \sum_I x_I \ln\left(\frac{\phi_I}{x_I}\right) \quad (58)$$

with $$\phi_I = \frac{x_I r_I}{\sum_J x_J r_J} \quad (59)$$

where $G^{ex,FH}$ is the Flory-Huggins term for the excess Gibbs energy, $\phi_I$ is the segment fraction of component I, and $r_I$ is the number of all conceptual segments in component I:

$$r_I = \sum_m r_{m,I} + r_{c,I} + r_{a,I} \quad (60)$$

The activity coefficient of component I from the combinatorial term can be derived from Eq. 60:

$$\ln \gamma_I^{FH} = \ln\left(\frac{\phi_I}{x_I}\right) + 1 - r_I \sum_J \frac{\phi_J}{r_J} = \ln\left(\frac{r_I}{\sum_J x_J r_J}\right) + 1 - \frac{r_I}{\sum_J x_J r_J} \quad (61)$$

The infinite-dilution activity coefficient of a component in water is:

$$\ln \gamma_I^{\infty FH} = \ln\left(\frac{r_I}{r_W}\right) + 1 - \frac{r_I}{r_W} \quad (62)$$

In both NRTL-SAC (parent patent application) and present invention eNRTL-SAC, water is selected as the reference for the hydrophilic segment z. Therefore, one can set $r_W=1$. Thus, one has:

$$\ln \gamma_I^{\infty FH} = \ln r_I + 1 - r_I \quad (63)$$

One can then compute the unsymmetric activity coefficient from the Flory-Huggins term as follows:

$$\ln \gamma_I^{*,FH} = \ln \gamma_I^{FH} - \ln \gamma_I^{\infty FH} = r_I - \ln\left(\sum_J x_J r_J\right) - \frac{r_I}{\sum_J x_J r_J} \quad (64)$$

NRTL Binary Parameters

In Eqs. 3 and 4 for NRTL-SAC, the model formulation requires the asymmetric interaction energy parameters, $\tau$, and the symmetric nonrandom factor parameters, $\alpha$, for each binary pair of the conceptual segments. In Eqs. 25-27 for eNRTL-SAC of the present invention, one needs additional binary parameters of $\tau$ and $\alpha$ between conceptual molecular segments, m and ionic segments, c or a. In practice, Applicants fix the values of $\alpha$'s for the binary pairs of molecular segment and ionic segment to the single value of 0.2 while the values of $\tau$ for the binary pairs of molecular segment and ionic segment are calculated from the $\tau$'s for the binary pairs of molecular segment and electrolyte segment. Following the same scheme in generalized eNRTL (Chen and Song, 2004b above), one can calculate these binary interaction energy parameters as follows:

$$\tau_{cm} = \tau_{am} = \tau_{em} \quad (65)$$

$$\tau_{mc,ac} = \tau_{ma,ca} = \tau_{me} \quad (66)$$

Following the treatment of NRTL-SAC (disclosed in U.S. application Ser. No. 10/785,925), Applicants identify a reference electrolyte for the conceptual electrolyte segment e. In searching for the reference electrolyte, Applicants choose one elemental electrolyte that has abundant literature data. In one example study, NaCl is used as the reference electrolyte for e. The ionic radii for sodium ion and chloride ion are $1.680 \times 10^{-10}$ m and $1.937 \times 10^{-10}$ m, respectively. With NaCl as the reference electrolyte, the energy parameters for the z-e pair are set to (8.885, −4.549) for the water-NaCl pair. The energy parameters for the x-e pair are set to (15, 5), in line with the parameters identified for $C_2H_4$—NaCl pair earlier by Chen and Song (Chen, 2004b). The energy parameters for the y-e pairs are set to (12, −3) after limited trials to optimize the performance of the model in this study. The complete set of NRTL binary interaction energy parameters are given in Table 2. Other choices of the reference electrolyte and parameter values may be suitable. The below reports the general behavior of the present invention eNRTL-SAC model based on the parameters reported in Table 2.

The electrolyte segment e is the only extra molecular descriptor and the electrolyte parameter E is the only extra molecular parameter for all electrolytes, inorganic or organic. All local and long range interactions derived from the existence of cationic and anionic species of various ionic charge valence, radius, chemical make-up, etc., are to be accounted for with this extra molecular descriptor for electrolytes together with combinations of conceptual molecular segments, i.e., hydrophobicity, polarity and hydrophilicity. In other words, every electrolyte, organic or inorganic, are modeled as combinations of E, X, Y, and Z. As such, electrolytes are recognized as "hydrophobic" electrolytes, "polar" electrolytes, "hydrophilic" electrolytes, and their various combinations. Likewise, ionic activity coefficient of each ionic species will be computed from its share of E, X, Y, and Z. The ions are to be considered as "hydrophobic" ions, "polar" ions, or "hydrophilic" ions.

FIGS. 1 to 5 show effects of the molecular parameters on mean ionic activity coefficients (mole fraction scale) of the reference electrolyte, i.e., electrolyte with E=1. As shown in FIGS. 1 to 5, hydrophobicity parameter X brings down the mean ionic activity coefficient at low electrolyte concentration but in a rather nonlinear way. Polarity parameter Y− raises the mean ionic activity coefficient while polarity parameter Y+ lowers the mean ionic activity coefficient. Hydrophilicity parameter Z has a relatively slight downshift effect on the mean ionic activity coefficient. Electrolyte parameter E brings down the mean ionic activity coefficient at low electrolyte concentration and pushes up the mean ionic activity coefficient at high electrolyte concentration.

Experimental data for ionic activity coefficients are not readily available though emerging (Wilczek-Vera, G. et al, "On the Activity of Ions and the Junction Potential: Revised Values for All Data," *AIChE J.*, 50:445, 2004). Given the fact that existing experimental data are limited to mean ionic activity coefficient for neutral electrolytes, Applicants are not able to directly identify the molecular parameters for ionic species. In preparing FIGS. 1 to 5 discussed above and the subsequent studies reported in the Model Applications section below, Applicants use Eqs. 17-18 to determine from electrolyte parameter E the ionic segment numbers for the ions and Applicants arbitrarily assign molecular segment parameters (X, Y−, Y+, and Z) only to the anion. This practice is acceptable since virtually all electrolytes investigated in this study are electrolytes with elemental cations.

Figure 14:
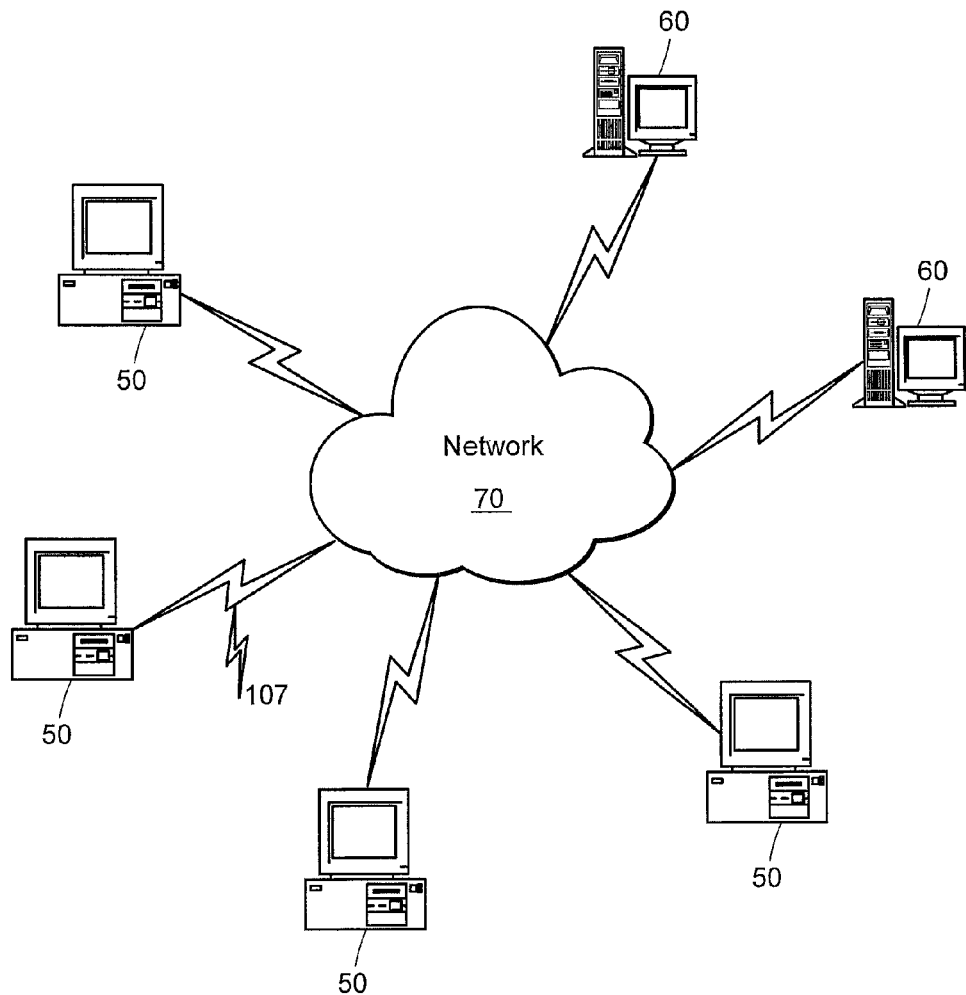
FIG. 14 is a schematic view of a computer network in which the present invention may be implemented.

Reference is now made to a preferred embodiment of the present invention as illustrated in FIGS. 14-17. FIG. 14 illustrates a computer network or similar digital processing environment in which the present invention may be implemented.

Referring to FIG. 14, client computer(s)/devices 50 and server computer(s) 60 provide processing, storage, and input/output devices executing application programs and the like. Client computer(s)/devices 50 can also be linked through communications network 70 to other computing devices, including other client devices/processes 50 and server computer(s) 60. Communications network 70 can be part of a remote access network, a global network (e.g., the Internet), a worldwide collection of computers, Local area or Wide area networks, and gateways that currently use respective protocols (TCP/IP, Bluetooth, etc.) to communicate with one another. Other electronic device/computer network architectures are suitable.

Figure 15:
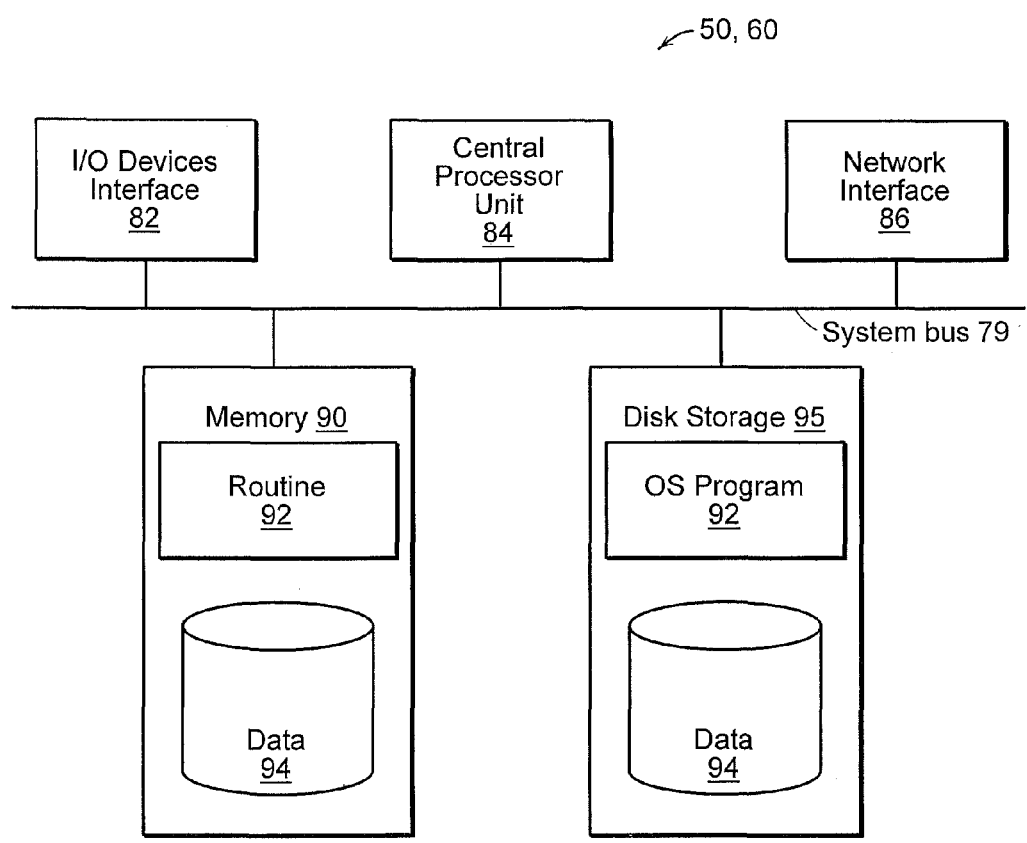
FIG. 15 is a block diagram of a computer of the network of FIG. 14.

FIG. 15 is a diagram of the internal structure of a computer (e.g., client processor/device 50 or server computers 60) in the computer system of FIG. 14. Each computer 50, 60 contains system bus 79, where a bus is a set of hardware lines used for data transfer among the components of a computer or processing system. Bus 79 is essentially a shared conduit that connects different elements of a computer system (e.g., processor, disk storage, memory, input/output ports, network ports, etc.) that enables the transfer of information between the elements. Attached to system bus 79 is I/O device interface 82 for connecting various input and output devices (e.g., keyboard, mouse, displays, printers, speakers, etc.) to the computer 50, 60. Network interface 86 allows the computer to connect to various other devices attached to a network (e.g., network 70 of FIG. 14). Memory 90 provides volatile storage for computer software instructions 92 and data 94 used to implement an embodiment of the present invention (e.g., eNRTL-SAC modeler 20 in FIGS. 16-17). Disk storage 95 provides non-volatile storage for computer software instructions 92 and data 94 used to implement an embodiment of the present invention. Central processor unit 84 is also attached to system bus 79 and provides for the execution of computer instructions.

In one embodiment, the processor routines 92 and data 94 are a computer program product (generally referenced 92 or 20), including a computer readable medium (e.g., a removable storage medium such as one or more DVD-ROM's, CD-ROM's, diskettes, tapes, etc.) that provides at least a portion of the software instructions for the invention system 20. Computer program product 92 can be installed by any suitable software installation procedure, as is well known in the art. In another embodiment, at least a portion of the software instructions may also be downloaded over a cable, communication and/or wireless connection. In other embodiments, the invention programs are a computer program propagated signal product 107 embodied on a propagated signal on a propagation medium (e.g., a radio wave, an infrared wave, a laser wave, a sound wave, or an electrical wave propagated over a global network such as the Internet, or other network (s)). Such carrier medium or signals provide at least a portion of the software instructions for the present invention routines/program 92.

In alternate embodiments, the propagated signal is an analog carrier wave or digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer readable medium of computer program product 92 (e.g., eNRTL-SAC modeler 20) is a propagation medium that the computer system 50 may receive and read, such as by receiving the propagation medium and identifying a propagated signal embodied in the propagation medium, as described above for computer program propagated signal product.

Generally speaking, the term "carrier medium" or transient carrier encompasses the foregoing transient signals, propagated signals, propagated medium, storage medium and the like.

Figure 16:
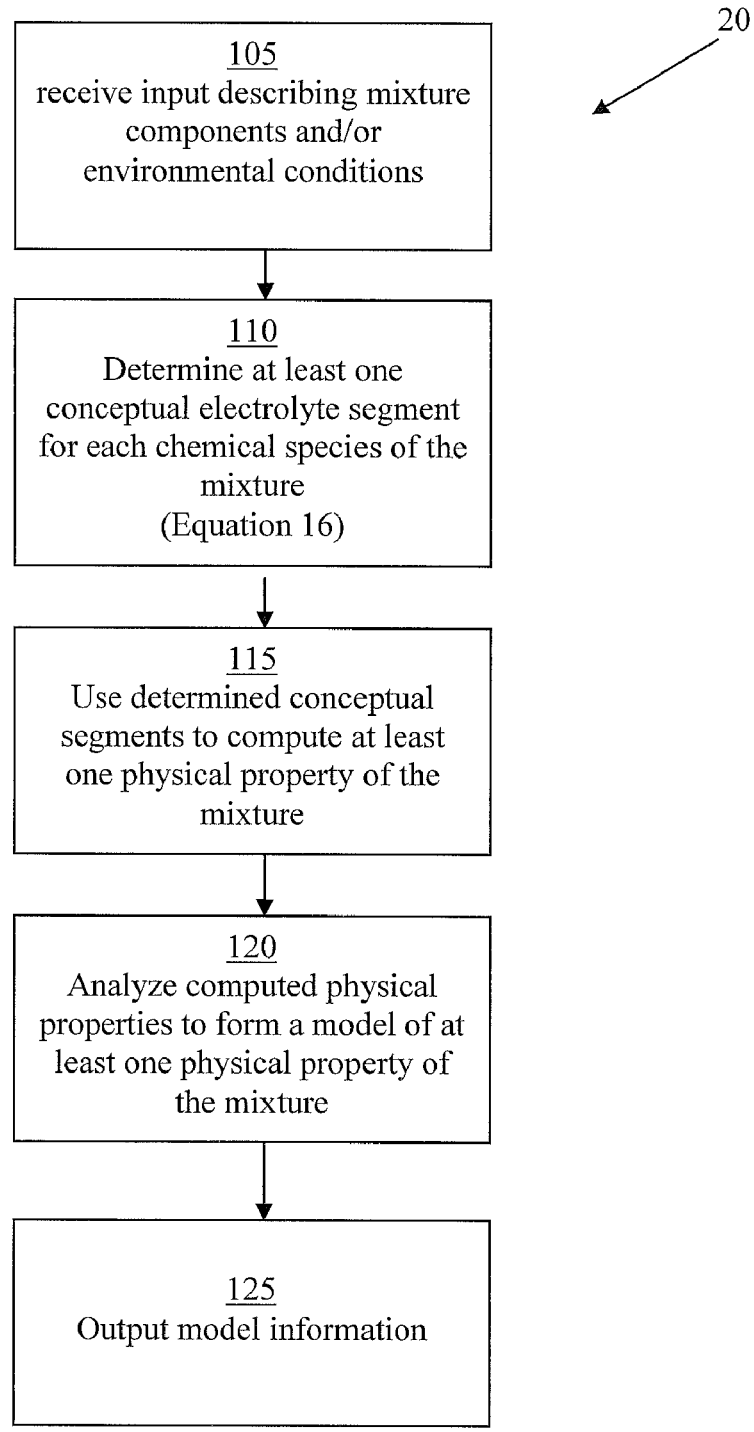
FIGS. 16-17 are flow diagrams of one embodiment of the present invention employed in the computer network environment of FIGS. 14 and 15.
Figure 17:
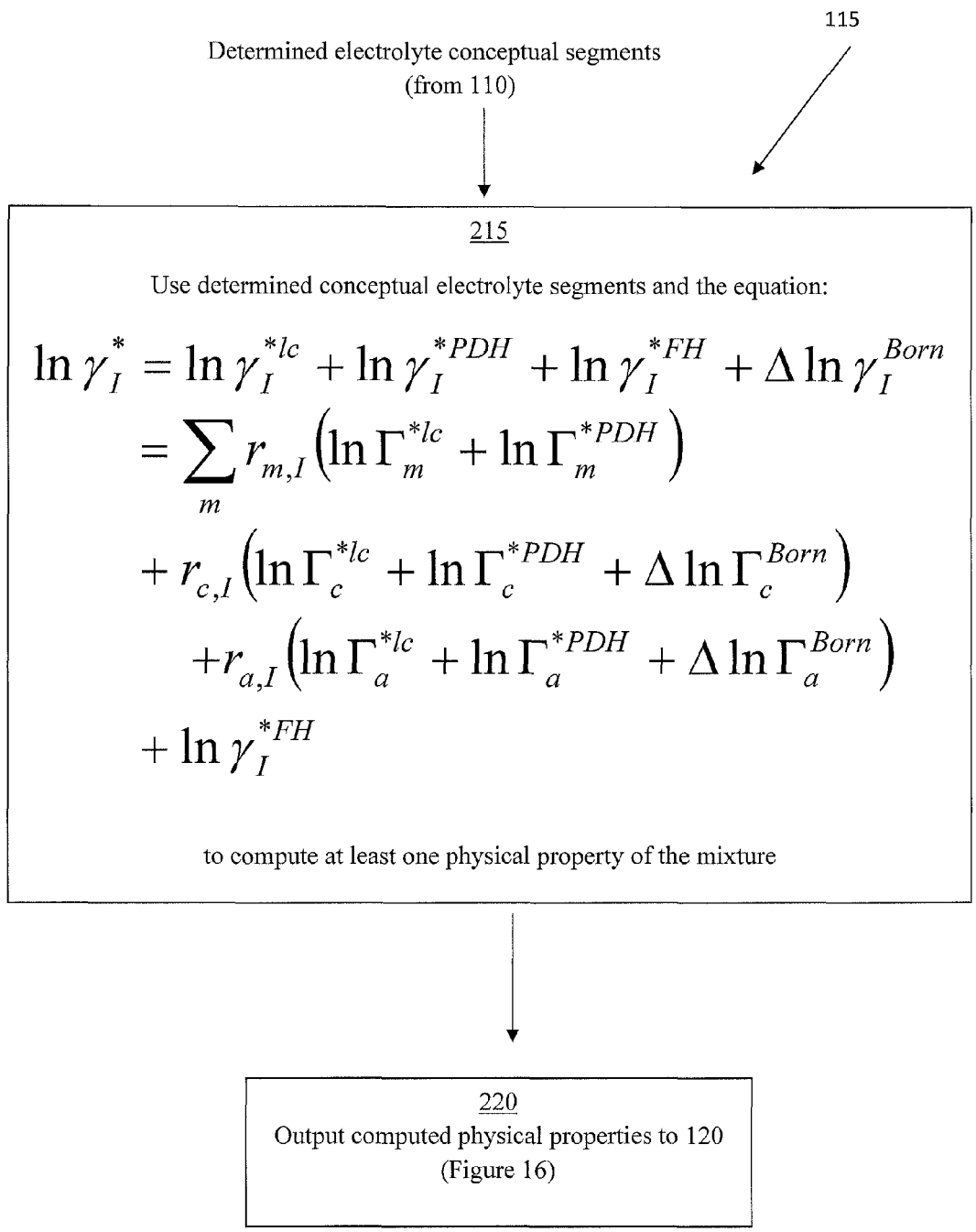

FIGS. 16 and 17 illustrate data flow and process steps for a modeler 20 performing the methods of the present invention. With reference to FIG. 16, chemical data describing one or more chemical species (e.g., an electrolyte and solvent) of the mixture and/or environmental conditions (e.g., pressure and/or temperature) is entered at step 105 of the modeler process. Step 110 uses that data and Equation 16 to determine at least one conceptual segment including a conceptual electrolyte segment for each of the chemical species of the mixture. The determined electrolyte conceptual segment and other determined conceptual segments are used to compute at least one physical property of the mixture during step 115. The computed physical properties are analyzed to form a model of at least one physical property of the mixture (e.g., solubility of one or more chemical species in one or more phases of the mixture) in step 120. The model information is then given as output at step 125. The output can take the form of data or an analysis appearing on a computer monitor, data or instructions sent to a process control system or device, data entered into a data storage device, and/or data or instructions relayed to additional computer systems or programs.

FIG. 17 illustrates in more detail the computation at step 115 in FIG. 16. Step 115 begins with the receipt of determined conceptual electrolyte and other segments for each of the chemical species (e.g., electrolyte, solvent, etc.) of the mixture. The determined conceptual electrolyte and other segments and Equation 16 are used to compute at least one physical property of the mixture during step 215. The computed physical properties are provided as output 220 from computation step 215. In step 220, the computed physical properties are passed to step 120 of FIG. 16 for forming a model of the physical property of the mixture as described above.

According to the foregoing, in some embodiments, the present invention 20 features a computer system for modeling at least one physical property of a mixture of at least two chemical species (e.g., an electrolyte dissolved in a liquid component/solvent. The computer system is formed of a user input means for determining chemical data from a user, a digital processor coupled to receive input from the input means, and an output means coupled to the digital processor. The digit processor hosts and executes a modeling system 20 in working memory. The modeling system 20 (i) uses the chemical data to determine one or more conceptual segments including a conceptual electrolyte segment for each of the chemical species; (ii) uses the determined conceptual segments to compute at least one physical property of the chemical mixture; and (iii) provides an analysis of the computed physical property. The analysis forms a model of the at least one physical property of the mixture. The output means provides to the user the formed model of the physical property of the chemical mixture.

In some embodiments, the present invention features a chemical compound manufactured by a process that includes a modeling method 20. The modeling method 20 models at least one physical property of a mixture of at least one electrolyte and one or more solvents. The invention method 20 comprises the computer implemented steps of (i) determining at least a conceptual electrolyte segment for the electrolyte solute, (ii) using the determined conceptual electrolyte segment computing at least one physical property of the mixture; and (iii) providing an analysis of the computed physical property. The step of determining at least a conceptual electrolyte segment may further include determining other conceptual segments and defining an identity and an equivalent number of each conceptual segment. The provided analysis forms a model of at least one physical property of the mixture.

Model 20 Applications

The following Examples are illustrative of the invention, and are not meant to be limiting in any way.

Limited amount of mean ionic activity coefficient data are available in the public literature for aqueous electrolytes. Applicants test the present eNRTL-SAC model 20 against mean ionic activity coefficient data of aqueous electrolyte systems. In addition, Applicants test the model 20 against salt solubility data in multiple solvents for a number of inorganic electrolytes and organic electrolytes. To the best of Applicants' knowledge, public literature data is very scarce for such salt solubility data. Proprietary solubility data from industrial collaborators was also used to test the applicability of the present invention model 20. However, results with such proprietary solubility data are not included in this discussion.

Mean Ionic Activity Coefficients in Aqueous Systems

For an electrolyte CA that dissociates to cation C and anion A, the mean ionic activity coefficients $\gamma^*_{\pm}$ is related to individual ionic activity coefficients as follows:

$$\ln \gamma^*_{\pm} = \frac{1}{\nu}(\nu_C \ln \gamma^*_C + \nu_A \ln \gamma^*_A) \tag{67}$$

where $\nu = \nu_C + \nu_A$.

Equation 67 gives the mean ionic activity coefficient on the mole fraction scale and it can be converted to the molality scale:

$$\ln \gamma^*_{\pm m} = \ln \gamma^*_{\pm} - \ln(1 + \nu m M_S/1000) \tag{68}$$

where $\gamma^*_{\pm m}$ is the mean ionic activity coefficient on the molality scale, m is the molality of the salt (mol/kg-solvent), and $M_S$ is the molecular weight of the solvent (g/mol).

Table 3 shows the fit to molality scale mean ionic activity coefficient data and the identified electrolyte and molecular parameters for the aqueous inorganic and organic electrolytes at 298.15 K as compiled by of Robinson and Stokes (1970) cited above. All mean ionic activity coefficient data are assumed to have standard deviation of 5%. The data for C5 and higher sodium carboxylates were excluded from the fit because these organic electrolytes were known to form micelles at high electrolyte concentrations (Chen, C.-C. et al., "Segment-Based Excess Gibbs Energy Model for Aqueous Organic Electrolytes, *AIChE J.*, 47:2593, 2001). With a few exceptions such as LiBr, most uni-univalent and uni-bivalent electrolytes are well represented as combinations of E and Y− or Y+ parameters. Most uni-univalent electrolytes have E parameter around unity while higher E values are found for higher valent electrolytes. Applicants also found that the fit seems to deteriorate for electrolytes with higher E values. This observation is consistent with the understanding that higher valent electrolytes are known to prone to the formation of hydrated species or other complexation species. The relatively poor representation of these electrolytes with the model reflects the inadequate assumption of complete dissociation for such electrolytes (Chen, C.-C.; et al., "Unification of Hydration and Dissociation Chemistries with the Electrolyte NRTL Model," *AIChE Journal*, 45:1576, 1999). As a derived property, mean ionic activity coefficient becomes meaningless if the complete dissociation assumption of electrolytes does not hold true.

Figure 6:
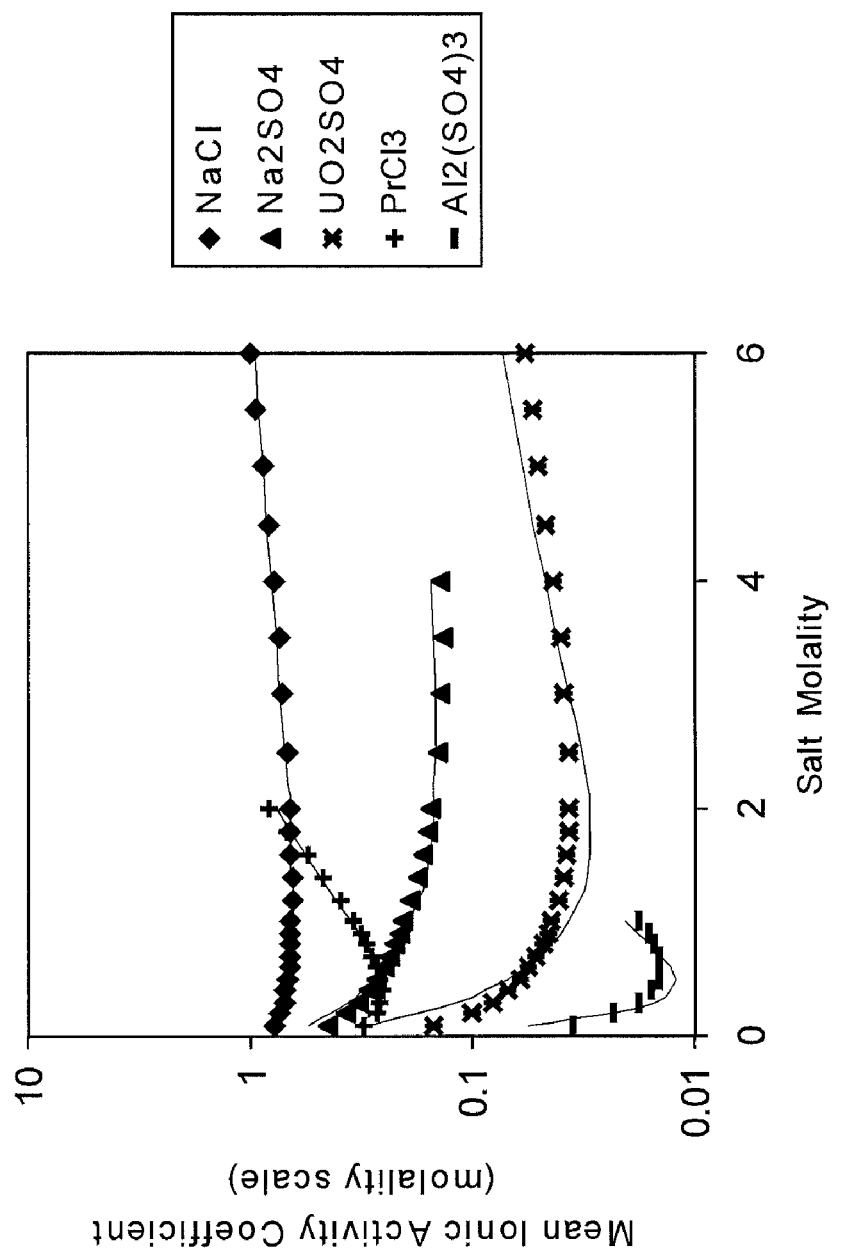
FIG. 6 is a graph illustrating comparison of experimental and calculated molality scale mean ionic activity coefficients of representative aqueous electrolytes at 298.15 K.

To illustrate the quality of the fit, FIG. 6 shows the comparison of experimental and calculated molality scale mean ionic activity coefficients for five aqueous electrolytes at 298.15 K. The solid lines are the calculated values from the model. It shows that the present invention eNRTL-SAC model 20 provides reasonable qualitative representation of the data while the original eNRTL model (Chen, C.-C. et al., "Local Composition Model for Excess Gibbs Energy of Electrolyte Systems," *AIChE J.*, 28:588, 1982) achieves excellent quantitative representation of the data.

Salt Solubility in Mixed Solvent Systems

At the solubility limit of a nonelectrolytes, the solubility product constant, $K_{sp}$, can be written in terms of the product of the solute concentration and the solute activity coefficient at the saturation concentration:

$$K_{sp} = x_I \gamma_I \quad (69)$$

At the solubility limit of an electrolyte, ionic species precipitate to form salt.

$$\nu_C C^{z_C} + \nu_A A^{z_A} \rightarrow C_{\nu_C} A_{\nu_A}(s) \quad (70)$$

The corresponding solubility product constant can be defined as follows.

$$K_{sp} = x_C^{\nu_C} \gamma_C^{*\nu_C} x_A^{\nu_A} \gamma_A^{*\nu_A} \quad (71)$$

Eqs. 70 and 71 can be expanded to include solvent molecules and other species if the solid polymorph involves hydrates, other solvent-containing salts, double salts, triple salts, and others.

Applicants tested the applicability of present invention eNRTL-SAC model 20 with the very limited public literature data and some proprietary data on solubilities of a number of inorganic and organic electrolytes in various solvents. This description presents the results with solubility data from public literature. To bring certain consistency to the data treatment, Applicants convert all solute solubility data to mole fraction (except for sodium chloride and sodium acetate). Applicants also assign standard deviation of 10% to all solute solubility data within range of 1 to 0.1, standard deviation of 20% to all solute solubility data with range of 0.1 to 0.01, standard deviation of 30% to data with range of 0.01 to 0.001, and so on.

Figure 7:
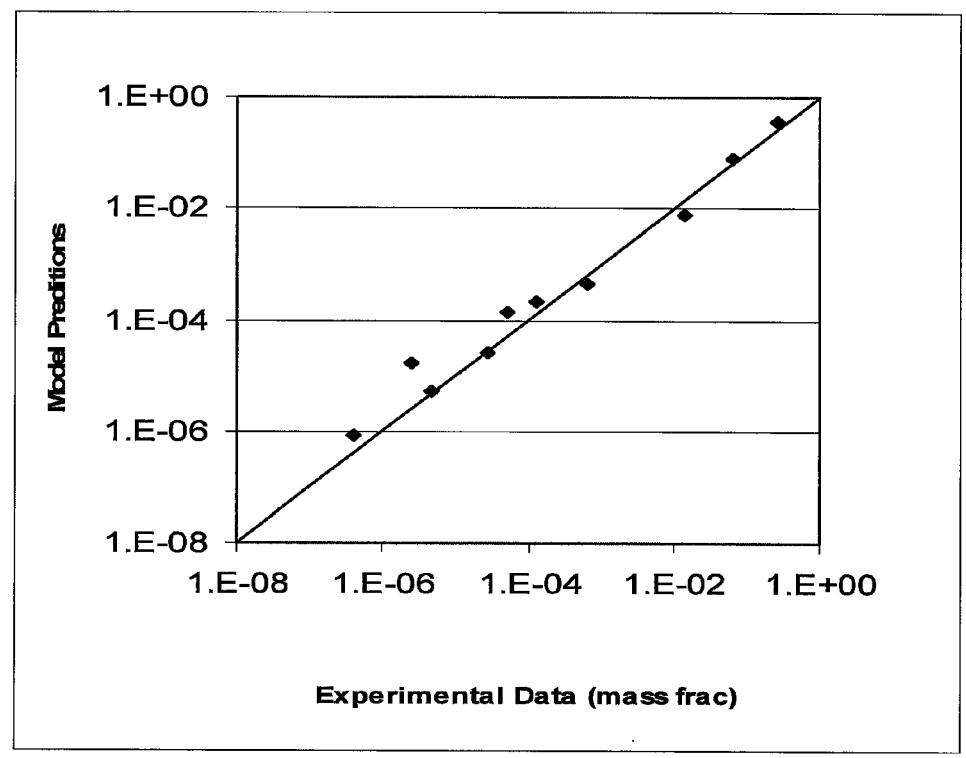
FIG. 7 is a graph illustrating the present invention model results for sodium chloride solubility at 298.15 K.

Solubility data of sodium chloride in twelve different solvents at 298.15 K were successfully fitted with the present invention model 20. (Note that the temperature for the acetone data is 291.15 K and the temperature for the ethyl acetate data is 292.15 K. However, they are included as if they were data at 298.15 K.) The sodium chloride solubilities in the twelve solvents vary by six orders of magnitude. The satisfactory fit of the data for ten solvents (formic acid and ethyl acetate excluded) is shown in FIG. 7. The present invention model 20 predicts one order-of-magnitude higher solubility for sodium chloride in formic acid and virtually no solubility for sodium chloride in ethyl acetate while the data suggests very low but measurable solubility. The molecular parameters and the solubility product constant were adjusted simultaneously to provide the best fit to the data and the identified values are given in Table 4. In Table 4, the last column to the right quantifies goodness of fit to data. It is worth noting that the electrolyte parameter E for sodium chloride is near unity, similar to the parameters reported in Table 3 for sodium chloride.

Figure 8:
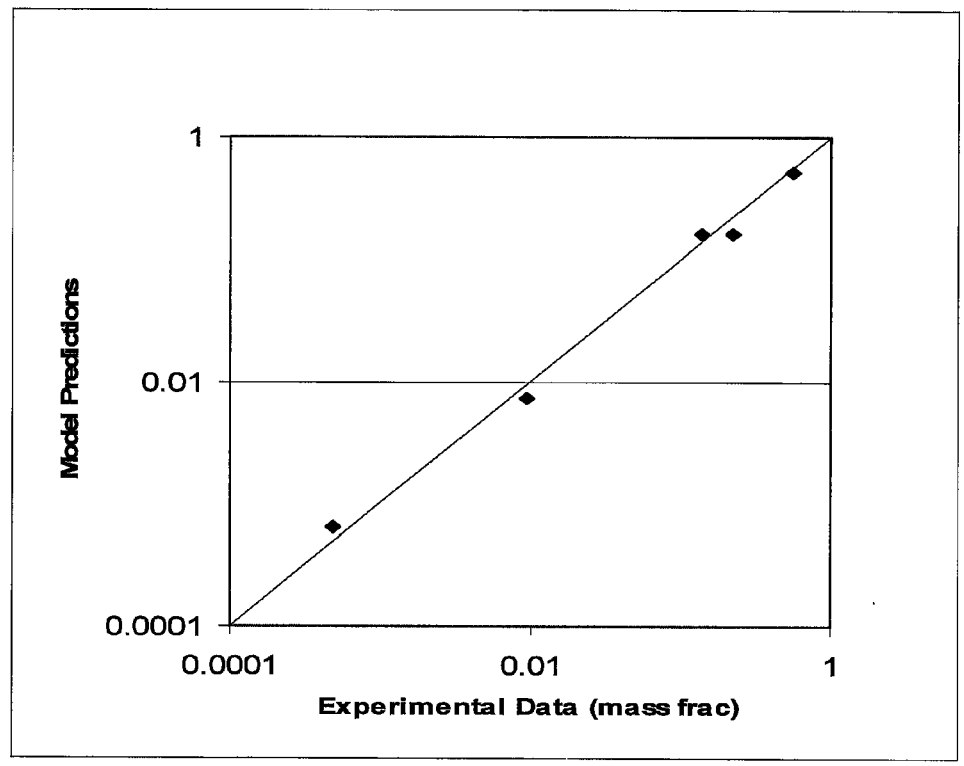
FIG. 8 is a graph illustrating the present invention model results for sodium acetate solubility at 298.15 K.

Solubility data of sodium acetate in five different solvents was also fitted successfully with the present invention model 20. The solubilities in the five solvents vary by four orders of magnitude. The fit of the data is shown in FIG. 8. The solid phase for the solubility measurements is anhydrous sodium acetate. Note that the data for methanol and acetone was taken at 291.15 K while the data for water and ethylene glycol was taken at 298.15 K. The temperature for the 1-propanol data is not known. In fitting the data, Applicants treated all data as if it was 298.15 K data. The identified molecular parameters and the solubility product constant are given in Table 4. As an organic electrolyte, the electrolyte parameter E for sodium acetate is found to be significantly less than unity.

Figure 9A:
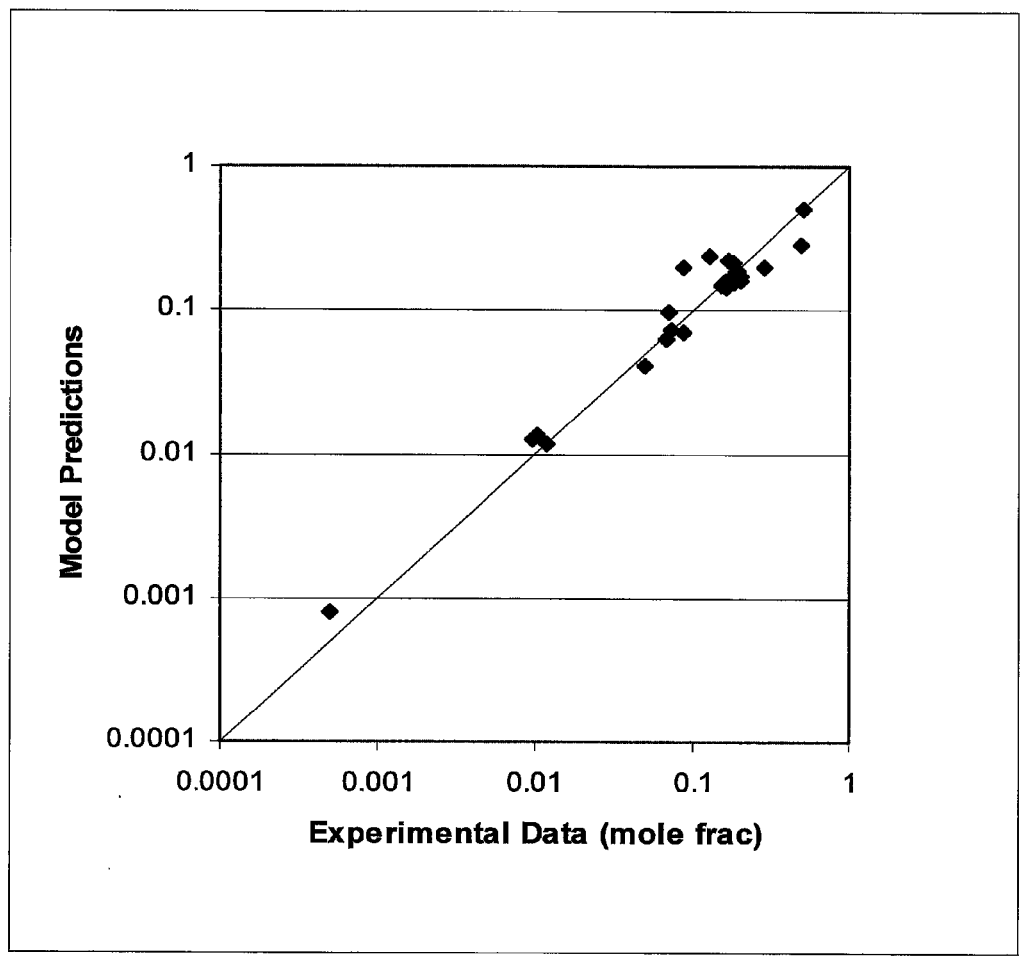
FIG. 9a is a graph illustrating the present invention model results for benzoic acid solubility at 298.15 K.
Figure 9B:
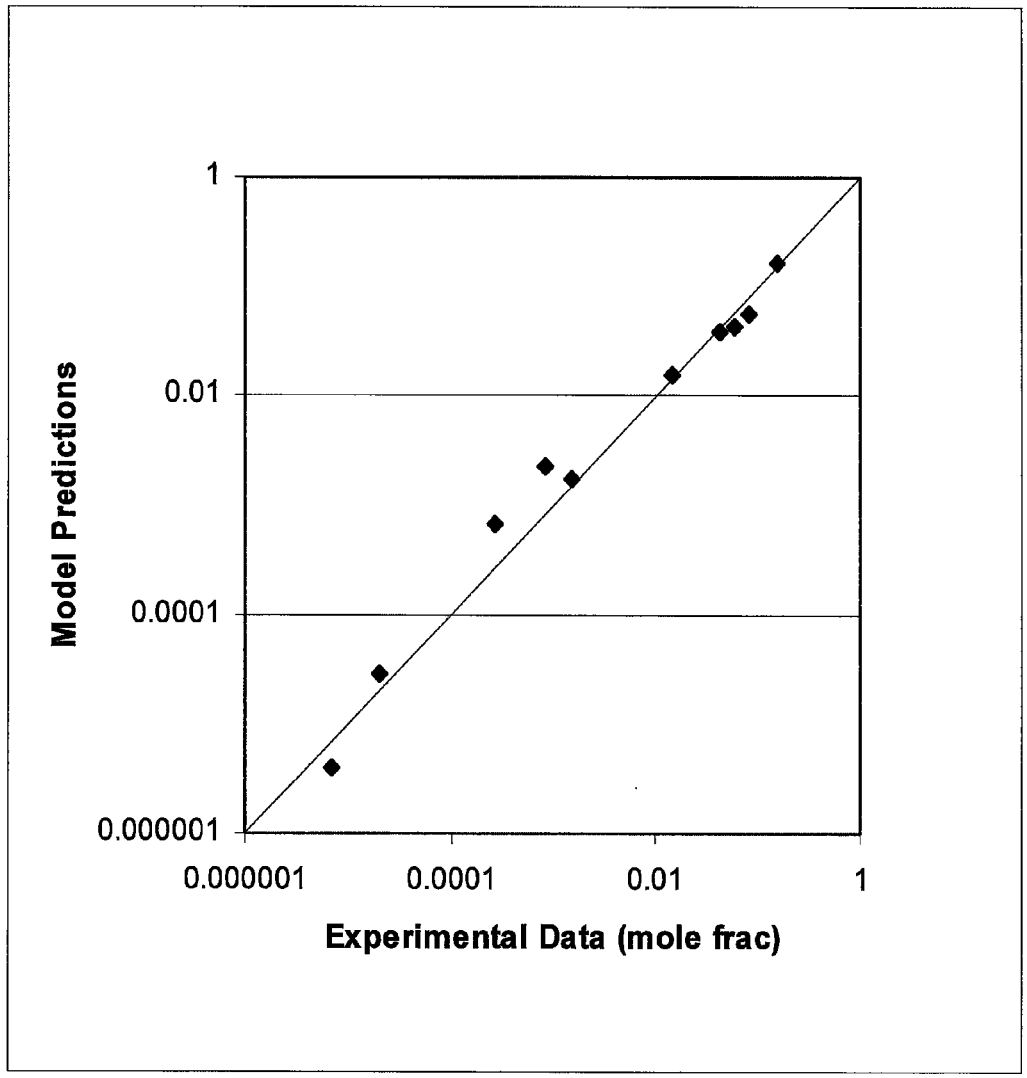
FIG. 9b is a graph illustrating the present invention model results for sodium benzoate solubility at 298.15 K.

FIGS. 9*a* and 9*b* show satisfactory representations of the solubility data of benzoic acid in twenty-six solvents (Beerbower, A. et al., "Expanded Solubility Parameter Approach. I. Naphthalene and Benzoic Acid in Individual Solvents," *J. Pharm. Sci.*, 73:179, 1984) and the solubility data of sodium benzoate in ten solvents (Bustamante, P. et al., "The Modified Extended Hansen Method to Determine Partial Solubility Parameters of Drugs Containing a Single Hydrogen Bonding Group and Their Sodium Derivatives: Benzoic Acid/Na and Ibuprofen/Na," *Int. J. of Pharmaceutics*, 194:117, 2000). These solvents are chosen in this study because of the availability of the NRTL-SAC parameters for the solvents from Applicants' prior work. The identified molecular parameters for the two solutes were given in Table 4. It is interesting that the molecular parameters identified for benzoic acid with twenty-six solvents in this study are quite similar to the molecular parameters identified for benzoic acid with seven solvents in Applicants' earlier study. Applicants also noted that the solubility range expands as benzoic acid is converted to sodium benzoate. Furthermore, the molecular parameters have changed from a hydrophobic/polar/hydrophilic combination (benzoic acid) to a polar/hydrophilic/electrolytic combination (sodium benzoate). Solubility data of sodium benzoate in seven other solvents (chloroform, benzene, dioxane, cyclohexane, ethyl acetate, heptane and chlorobenzene) is excluded from FIG. 9*b* because the present invention model 20 predicts virtually no solubility for sodium benzoate in these solvents while the data suggests very low but measurable solubility. It is probable that the molecular form of sodium benzoate may be present in such highly hydrophobic solvents. However, due to their low concentrations, Applicants chose to ignore these low solubility solvents in this study although the current thermodynamic framework can be used to account for the two solubility routes, i.e., Eqs. 69 and 71, individually or simultaneously.

Figure 10A:
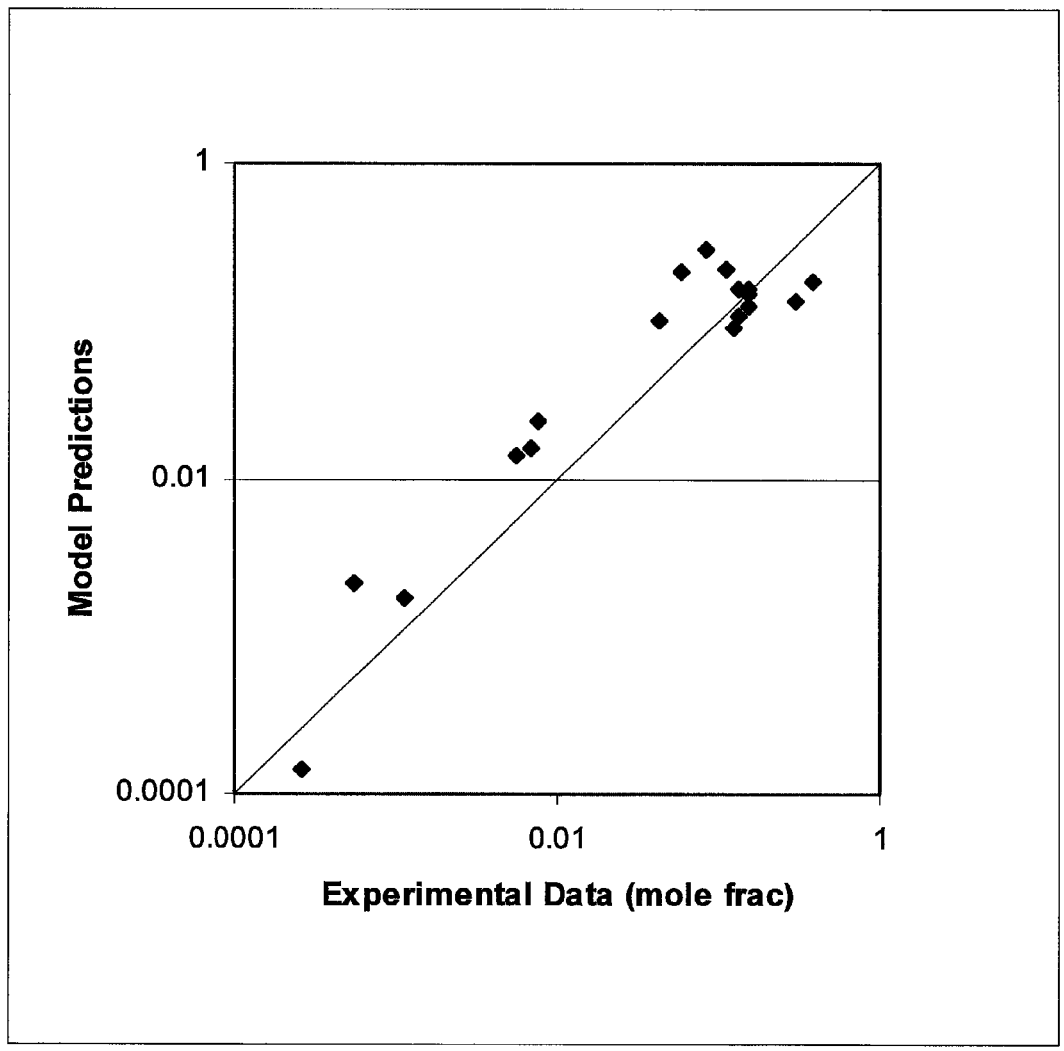
FIG. 10a is a graph illustrating the present invention model results for salicylic acid solubility at 298.15 K.
Figure 10B:
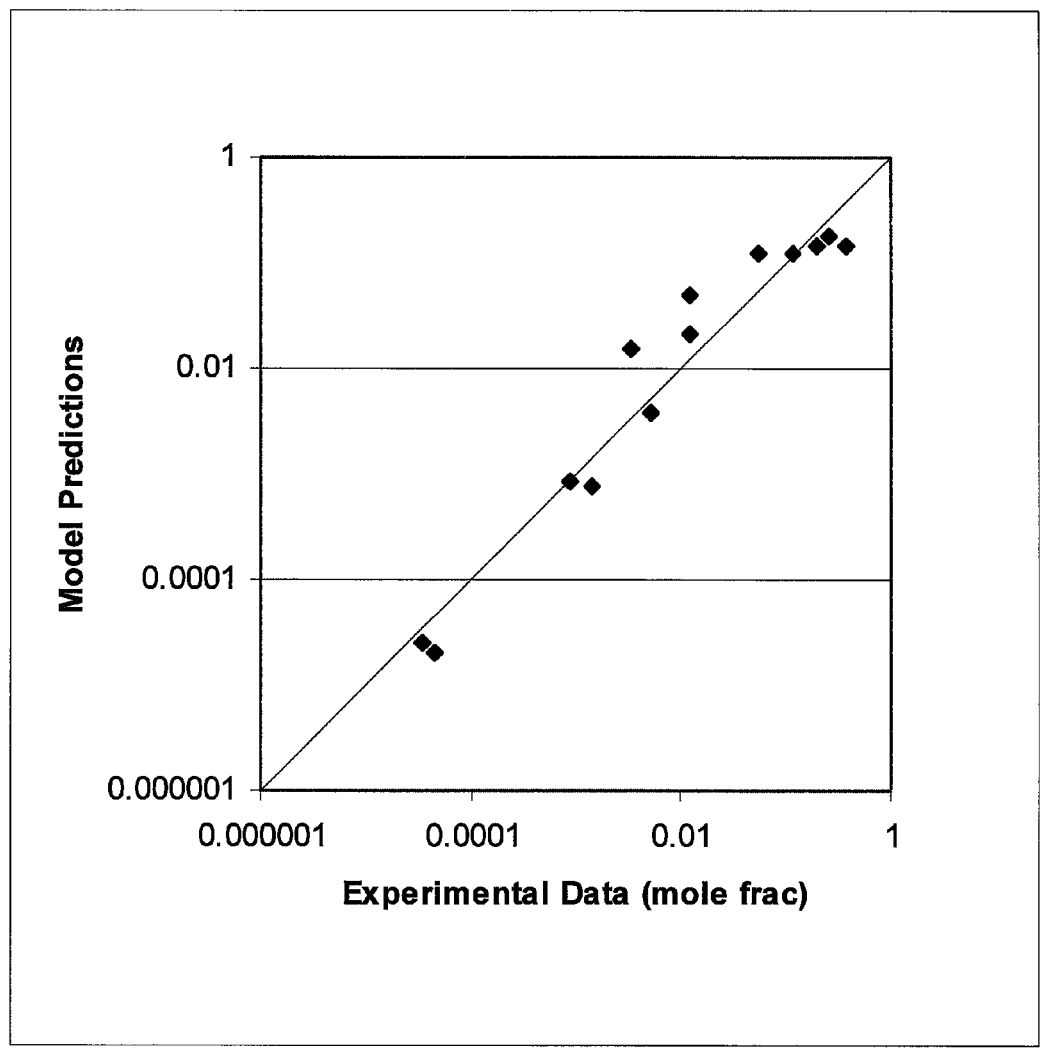
FIG. 10b is a graph illustrating the present invention model results for sodium salicylate solubility at 298.15 K.

FIGS. 10*a* and 10*b* show successful representations of the solubility data of salicylic acid in eighteen solvents and the solubility data of sodium salicylate in thirteen solvents (Barra, J. et al., "Proposition of Group Molar Constants for Sodium to Calculate the Partial Solubility Parameters of Sodium Salts Using the van Krevelen Group Contribution Method," *Eur. J. of Pharm. Sci.*, 10:153, 2000). Their molecular parameters were given in Table 4. Like the molecular parameters for benzoic acid and the sodium salt, the molecular parameters have changed from a hydrophobic/polar/hydrophilic combination (salicylic acid) to a polar/hydrophilic/electrolytic combination (sodium salicylate). Solubility data of sodium salicylate in benzene, cyclohexane, and heptane is excluded from FIG. 10*b*, again because the present invention model 20 predicts virtually no solubility of sodium salicylate in these three solvents although the data suggests very low but measurable solubility. Acetic acid is the only outlier among solvents with significant solubility for sodium salicylate. The present invention model 20 prediction for the solubility of sodium salicylate in acetic acid is about one order of magnitude too high. Acetic acid is not included in the thirteen solvents shown in FIG. 10b.

Figure 11A:
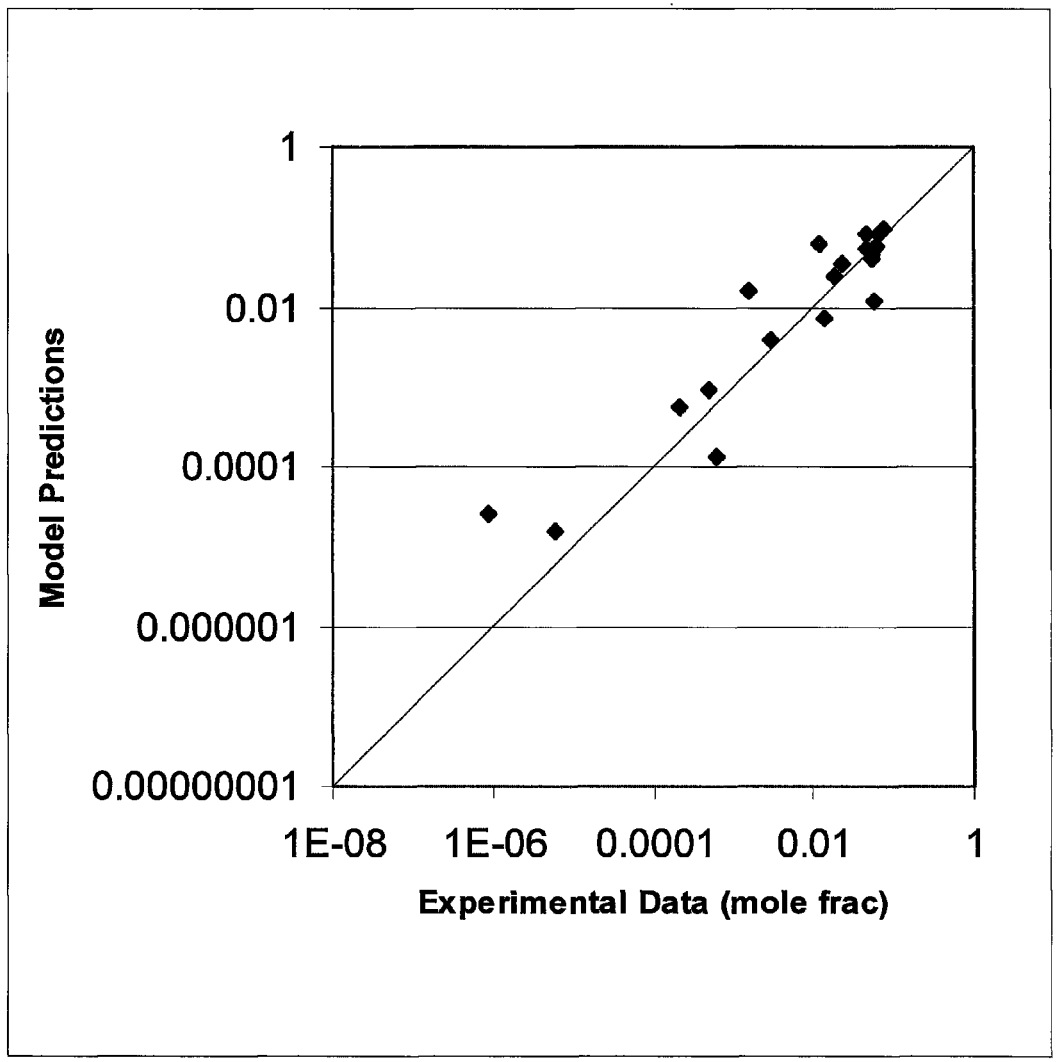
FIG. 11a is a graph illustrating the present invention model results for p-aminobenzoic acid solubility at 298.15 K.
Figure 11B:
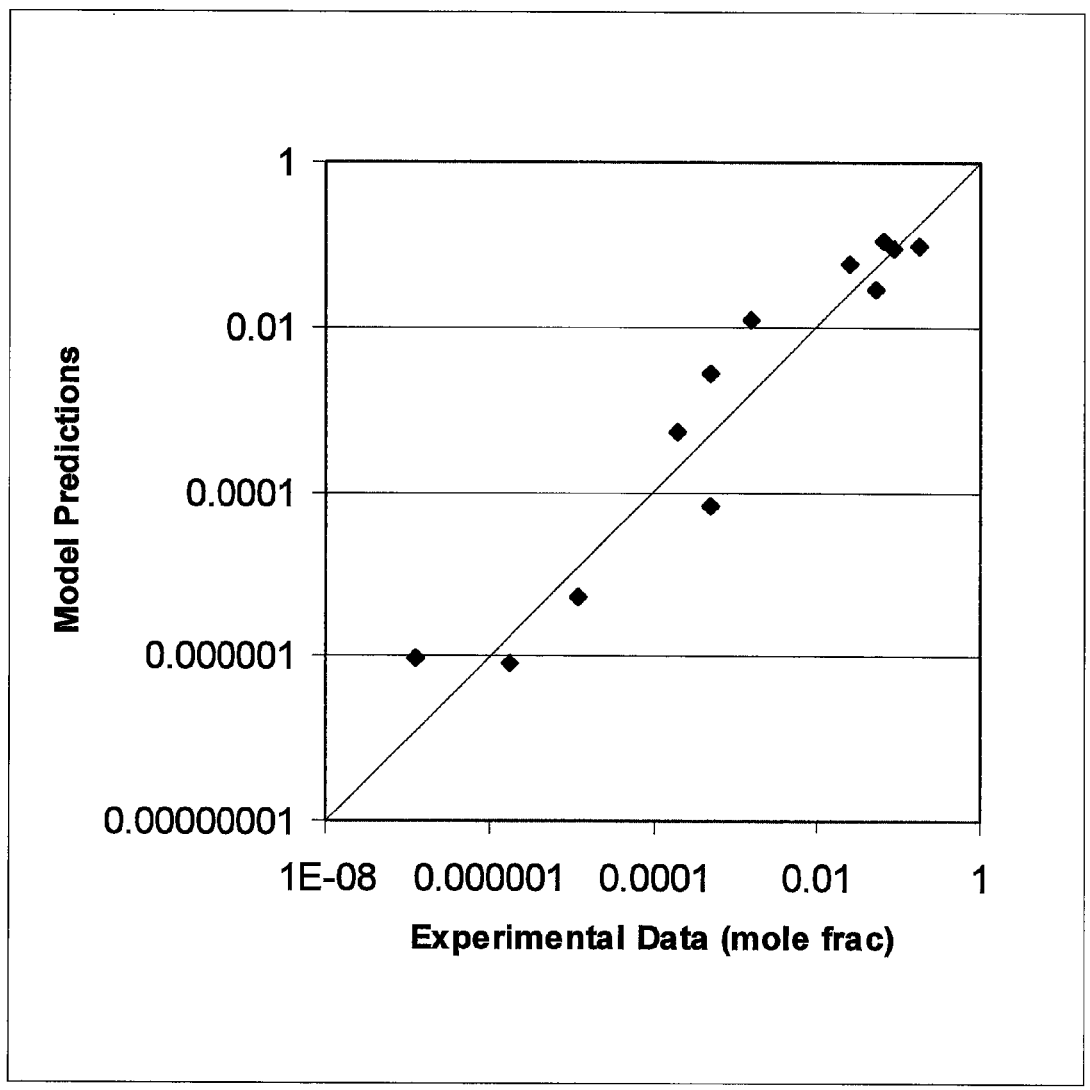
FIG. 11b is a graph illustrating the present invention model results for sodium p-aminobenzoate solubility at 298.15 K.

The present invention model 20 results for the solubility data of p-aminobenzoic acid in nineteen solvents and sodium p-aminobenzoate in twelve solvents (Barra et al., 2000, above) are given in FIGS. 11a and 11b. Again, low solubility solvents (benzene, cyclohexane and heptane) are excluded from FIG. 11b for sodium aminobenzoate. Acetone and DMF are two outliers for sodium aminobenzoate and they are also excluded from FIG. 11b. The present invention model 20 predicts two orders of magnitude higher solubilities in these two solvents.

Figure 12A:
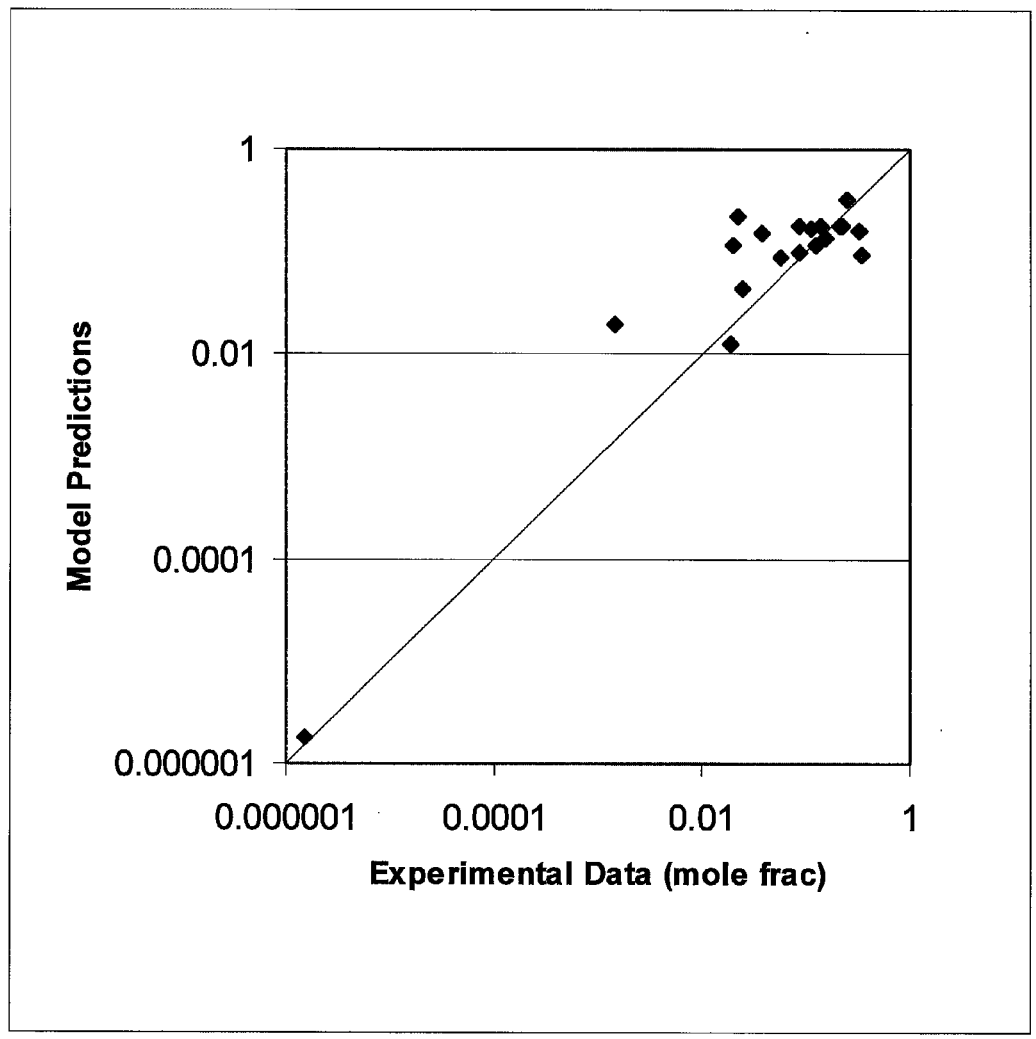
FIG. 12a is a graph illustrating the present invention model results for ibuprofen solubility at 298.15 K
Figure 12B:
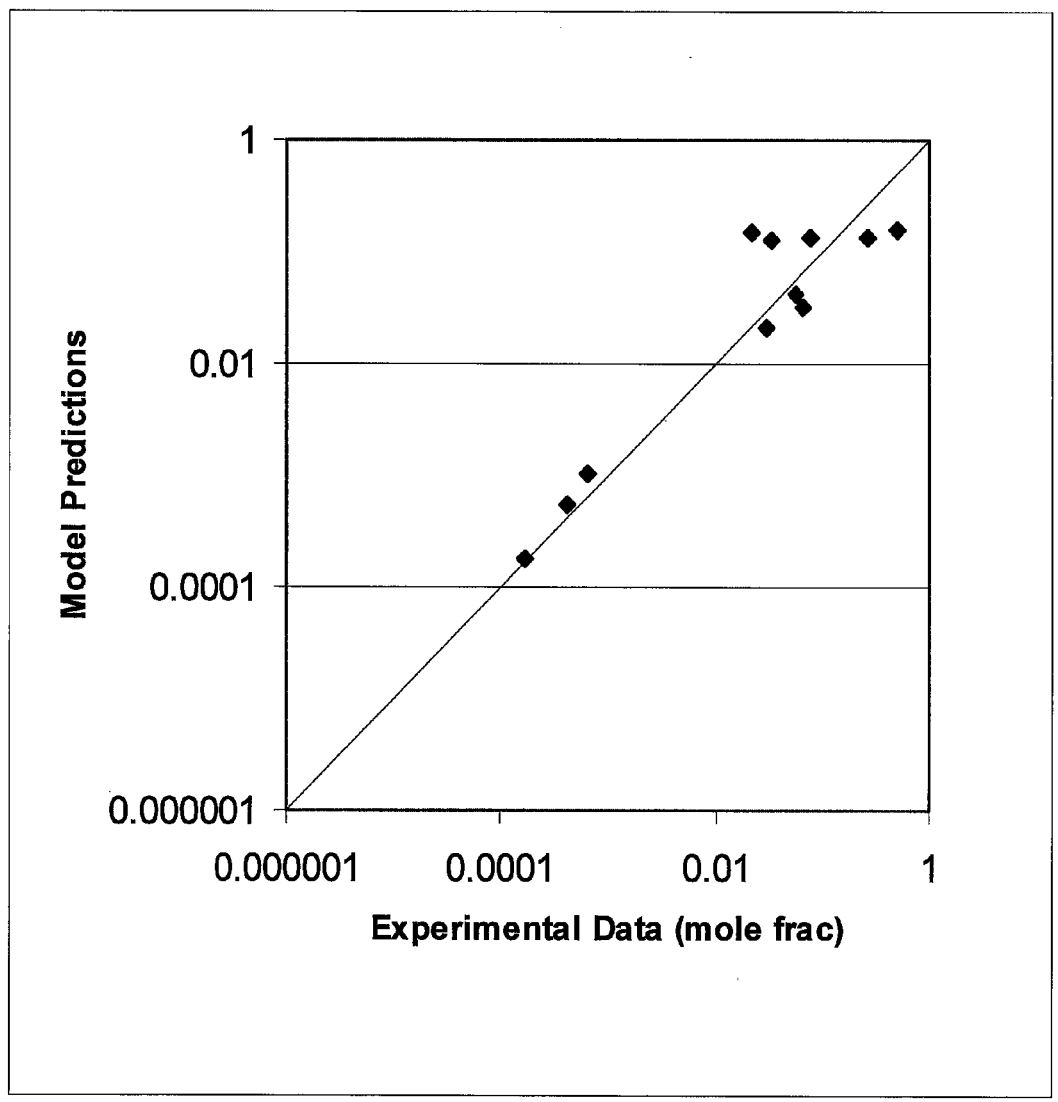
FIG. 12b is a graph illustrating the present invention model results for sodium ibuprofen solubility at 298.15 K.

The solubility data and model calculations for ibuprofen in nineteen solvents and sodium ibuprofen in eleven solvents (Bustamante et al., 2000 above) are given in FIGS. 12a and 12b. In comparison to other organic solutes, one embodiment of the model 20 provides a rather poor fit to the ibuprofen data albeit a better fit than in prior nonelectrolyte models. Applicants did notice that the ibuprofen solubility data from Bustamante et al. are significantly different from those reported by Gracin and Rasmuson (Gracin, S. and A. C. Rasmuson, "Solubility of Phenylacetic Acid, p-Hydroxyphenylacetic Acid, p-Aminophenylacetic acid, p-Hydroxybenzoic acid, and Ibuprofen in Pure Solvents," *J. Chem. Eng. Data,* 47:1379, 2002) for certain common solvents including methanol, ethanol, acetone and ethyl acetate. No attempt was made to reconcile the differences between the Bustamante data and the Gracin and Rasmuson data. The present invention model 20 fit to the sodium ibuprofen solubility data appears to be more satisfactory. Again, the eleven solvents reported in FIG. 12b do not include low solubility solvents (benzene, cyclohexane, heptane, and chlorobenzene). Similarly, acetone and DMF are two outliers for sodium ibuprofen and they are also excluded from FIG. 12b. The present invention model 20 predicts two orders of magnitude higher solubilities in these two solvents than the available data. Bustamante et al. (2000, above) reported high water content of the ibuprofen sample (3.3 wt % water) and the sodium ibuprofen sample (13 wt % water). It is not clear how such high water contents in the samples could impact on the solubility measurements.

Figure 13A:
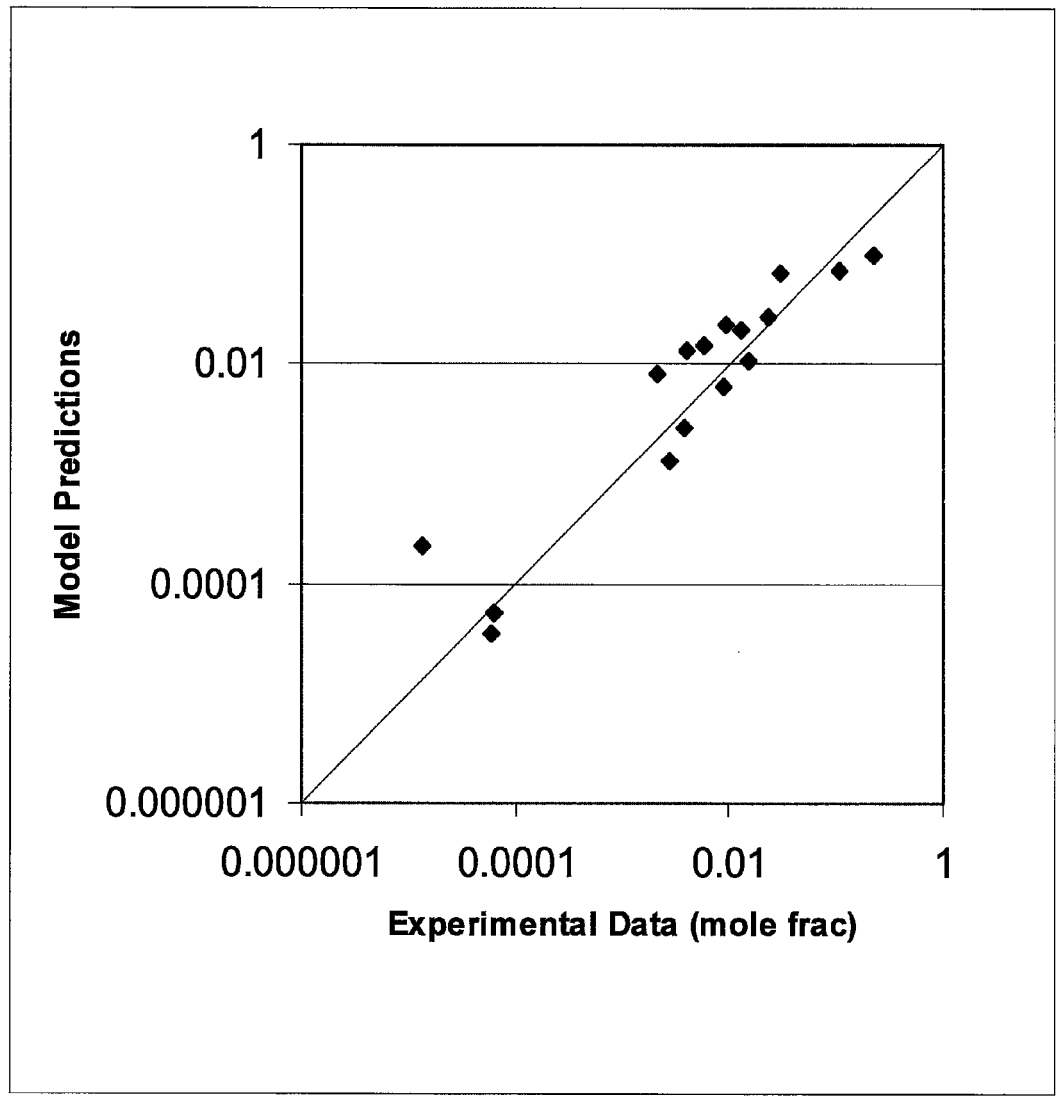
FIG. 13a is a graph illustrating the present invention model results for diclofenac solubility at 298.15 K.
Figure 13B:
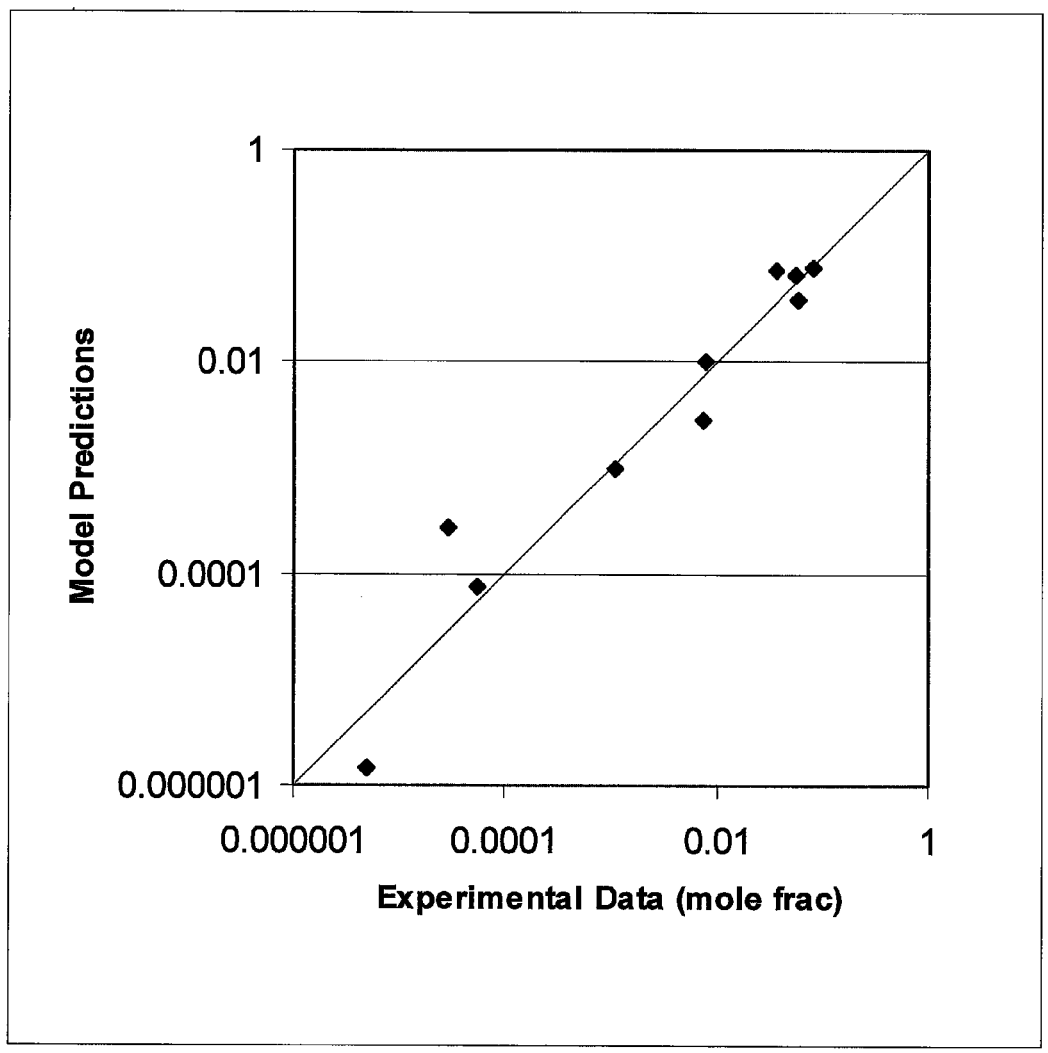
FIG. 13b is a graph illustrating the present invention model results for sodium diclofenac solubility at 298.15 K.

The solubility data for diclofenac in sixteen solvents and sodium diclofenac in ten solvents (Barra et al., 2000 above) are fitted and reported in FIGS. 13a and 13b. The present invention model 20 significantly overestimates the solubilities of diclofenac in acetic acid, formamide and ethylene glycol. These three solvents are excluded from the sixteen solvents shown in FIG. 13a. Data for low solubility solvents (benzene, cyclohexane, ethyl acetate, heptane and chlorobenzene) for sodium diclofenac are excluded from FIG. 13b. Acetic acid and acetone are two outliers with the model estimations one to three orders of magnitude higher solubilities for sodium diclofenac. The two solvents are not included in FIG. 13b.

The solubility data treatment above assumes complete dissociation of electrolytes and considers the solubility problem as formation of salts from ionized species of electrolytes, i.e., Eq. 71. One may argue that electrolytes do not dissociate completely into ionic species especially in organic solvents of low dielectric constant. In the absence of dissociation to ionic species, the solubility relationship can be described by Eq. 69 and the eNRTL-SAC model of the present invention reduces to the NRTL-SAC model of the parent patent application. Applicants have treated the electrolyte systems above as non-electrolytes (i.e., no dissociation to ionic species) with NRTL-SAC and the model results are also included in Table 4. With the absence of electrolyte parameter, the representation of the solubility data deteriorates substantially. Applicants also noted that the identified molecular parameters (X, Y−, Y+, and Z) with the complete dissociation treatment are roughly twice as large as those reported with the non-dissociation treatment. This finding is consistent with the fact that Applicants only assign the molecular parameters (X, Y−, Y+, and Z) to the anion.

TABLE 1

| Dielectric Constant of Solvents at 298.15 K | |
|---|---|
| solvent name | dielectric constant at 298.15 K |
| Acetic acid | 6.13 |
| Acetone | 20.83 |
| Acetonitrile | 36.97 |
| Anisole | 4.3 |
| Benzene | 2.27 |
| 1-Butanol | 17.7 |
| 2-Butanol | 15.8 |
| n-Butyl-acetate | 5.1 |
| Methyl-tert-butyl-ether | 2.6 |
| Carbon-tetrachloride | 2.23 |
| Chlorobenzene | 5.56 |
| Chloroform | 4.7 |
| Cumene | 2.22 |
| Cyclohexane | 2.02 |
| 1,2-Dichloroethane | 10.19 |
| 1,1-Dichloroethylene | 4.6 |
| 1,2-Dichloroethylene | 4.6 |
| Dichloromethane | 8.9 |
| 1,2-Dimethoxyethane | not available |
| N,N-Dimethylacetamide | not available |
| N,N-Dimethylformamide | 38.3 |
| Dimethyl-sulfoxide | 47.2 |
| 1,4-Dioxane | 2.21 |
| Ethanol | 24.11 |
| 2-Ethoxyethanol | not available |
| Ethyl-acetate | 6.02 |
| Ethylene-glycol | 41.2 |
| Diethyl-ether | 4.26 |
| Ethyl-formate | 7.16 |
| Formamide | 109.5 |
| Formic-acid | 58.5 |
| n-Heptane | 1.92 |
| n-Hexane | 1.89 |
| Isobutyl-acetate | 5.6 |
| Isopropyl-acetate | not available |
| Methanol | 32.62 |
| 2-Methoxyethanol | not available |
| Methyl-acetate | 6.68 |
| 3-Methyl-1-butanol | 14.7 |
| 2-Hexanone | 14.6 |
| Methylcyclohexane | 2.02 |
| Methyl-ethyl-ketone | 18.5 |
| Methyl-isobutyl-ketone | 13.1 |
| Isobutanol | 17.9 |
| N-Methyl-2-pyrrolidone | 33 |
| Nitromethane | 6.26 |
| n-Pentane | 1.84 |
| 1-Pentanol | 13.9 |
| 1-Propanol | 20.1 |
| Isopropyl-alcohol | 19.9 |
| n-propyl-acetate | 6 |
| Pyridine | 2.3 |
| Sulfolane | 43.3 |
| Tetrahydrofuran | 7.52 |
| 1,2,3,4-Tetrahydronaphthalene | not available |
| Toluene | 2.36 |
| 1,1,1-Trichloroethane | 7.5 |
| Trichloroethylene | 3.42 |
| m-Xylene | 2.24 |
| Water | 78.54 |
| Triethylamine | 2.44 |
| 1-Octanol | 10.3 |

TABLE 2

NRTL Binary Interaction Parameters

| | Segment (1) | | | | |
|---|---|---|---|---|---|
| | x | x | y− | y+ | x |
| | | | Segment (2) | | |
| | y− | z | z | z | y+ |
| $\tau_{12}$ | 1.643 | 6.547 | −2.000 | 2.000 | 1.643 |
| $\tau_{21}$ | 1.834 | 10.949 | 1.787 | 1.787 | 1.834 |
| $\alpha_{12}=\alpha_{21}$ | 0.2 | 0.2 | 0.3 | 0.3 | 0.2 |

| | Segment (1) | | | |
|---|---|---|---|---|
| | x | y− | y+ | z |
| | | | Segment (2) | |
| | e | e | e | e |
| $\tau_{12}$ | 15 | 12 | 12 | 8.885 |
| $\tau_{21}$ | 5 | −3 | −3 | −4.549 |
| $\alpha_{12}=\alpha_{21}$ | 0.2 | 0.2 | 0.2 | 0.2 |

TABLE 3

Results of Fit for Molality Scale Mean Ionic Activity Coefficient Data of Aqueous Electrolytes at 298.15K (Data from Robinson and Stokes, 1970)

| | E | Y− | Y+ | σ□ | max. molality |
|---|---|---|---|---|---|
| 1-1 Electrolytes | | | | | |
| $AgNO_3$ | 0.738 | | 1.758 | 0.050 | 6.0 |
| CsAc | 1.002 | 0.438 | | 0.011 | 3.5 |
| CsBr | 0.950 | | 0.678 | 0.013 | 5.0 |
| CsCl | 0.948 | | 0.643 | 0.014 | 6.0 |
| CsI | 0.956 | | 0.719 | 0.012 | 3.0 |
| $CsNO_3$ | 0.981 | | 1.328 | 0.005 | 1.4 |
| CsOH | 0.942 | 0.354 | | 0.002 | 1.0 |
| HBr | 1.135 | 0.654 | | 0.034 | 3.0 |
| HCl | 1.324 | 0.524 | | 0.087 | 6.0 |
| $HClO_4$ | 1.476 | 0.569 | | 0.136 | 6.0 |
| HI | 1.117 | 0.824 | | 0.035 | 3.0 |
| $HNO_3$ | 0.971 | 0.211 | | 0.005 | 3.0 |
| KAc | 0.998 | 0.386 | | 0.009 | 3.5 |
| KBr | 0.910 | | 0.311 | 0.011 | 5.5 |
| $KBrO_3$ | 0.968 | | 1.141 | 0.002 | 0.5 |
| KCl | 0.920 | | 0.370 | 0.010 | 4.5 |
| $KClO_3$ | 0.958 | | 1.053 | 0.003 | 0.7 |
| KCNS | 0.876 | | 0.477 | 0.019 | 5.0 |
| KF | 0.987 | | 0.042 | 0.004 | 4.0 |
| KH Malonate | 0.846 | | 0.920 | 0.022 | 5.0 |
| KH Succinate | 0.912 | | 0.665 | 0.011 | 4.5 |
| $KH_2PO_4$ | 0.970 | | 1.362 | 0.006 | 1.8 |
| KI | 0.903 | | 0.168 | 0.011 | 4.5 |
| $KNO_3$ | 0.856 | | 1.461 | 0.027 | 3.5 |
| KOH | 1.236 | 0.344 | | 0.058 | 6.0 |
| K Tol | 0.750 | | 1.296 | 0.026 | 3.5 |
| LiAc | 0.962 | 0.097 | | 0.002 | 4.0 |
| LiBr | 1.422 | 0.526 | | 0.116 | 6.0 |
| LiCl | 1.282 | 0.436 | | 0.084 | 6.0 |
| $LiClO_4$ | 1.145 | 0.681 | | 0.047 | 4.0 |
| LiI | 1.058 | 0.712 | | 0.033 | 3.0 |
| $LiNO_3$ | 1.050 | 0.294 | | 0.022 | 6.0 |
| LiOH | 1.028 | | 0.652 | 0.022 | 4.0 |
| LiTol | 0.881 | | 0.392 | 0.014 | 4.5 |
| NaAc | 0.978 | 0.301 | | 0.005 | 3.5 |
| NaBr | 0.992 | 0.115 | | 0.008 | 4.0 |
| $NaBrO_3$ | 0.923 | | 0.802 | 0.010 | 2.5 |
| Na Butyrate | 0.989 | 0.566 | | 0.009 | 3.5 |
| NaCl | 1.000 | | | 0.017 | 6.0 |
| $NaClO_3$ | 0.891 | | 0.507 | 0.011 | 3.5 |
| $NaClO_4$ | 0.894 | | 0.267 | 0.010 | 6.0 |
| NaCNS | 0.925 | 0.128 | | 0.006 | 4.0 |
| NaF | 0.976 | | 0.425 | 0.002 | 1.0 |
| Na Formate | 0.905 | | 0.094 | 0.013 | 3.5 |
| NaH Malonate | 0.878 | | 0.664 | 0.019 | 5.0 |
| NaH Succinate | 0.924 | | 0.495 | 0.010 | 5.0 |
| $NaH_2PO_4$ | 0.864 | | 1.256 | 0.020 | 6.0 |
| NaI | 1.009 | 0.266 | | 0.012 | 3.5 |
| $NaNO_3$ | 0.825 | | 0.842 | 0.029 | 6.0 |
| NaOH | 1.080 | 0.109 | | 0.039 | 6.0 |
| Na Propionate | 0.992 | 0.448 | | 0.006 | 3.0 |
| Na Tol | 0.793 | | 0.920 | 0.026 | 4.0 |
| $NH_4Cl$ | 0.884 | | 0.424 | 0.019 | 6.0 |
| $NH_4NO_3$ | 0.813 | | 1.128 | 0.043 | 6.0 |
| RbAc | 1.012 | 0.416 | | 0.011 | 3.5 |
| RbBr | 0.914 | | 0.519 | 0.016 | 5.0 |
| RbCl | 0.929 | | 0.466 | 0.012 | 5.0 |
| RbI | 0.925 | | 0.520 | 0.014 | 5.0 |
| $RbNO_3$ | 0.815 | | 1.611 | 0.038 | 4.5 |
| TlAc | 0.864 | | 0.952 | 0.033 | 6.0 |
| $TlClO_4$ | 1.020 | | 1.231 | 0.000 | 0.5 |
| $TlNO3$ | 1.069 | | 1.692 | 0.003 | 0.4 |
| 1-2 Electrolytes | | | | | |
| $Cs_2SO_4$ | 1.161 | | 2.568 | 0.050 | 1.8 |
| $K_2CrO_4$ | 1.048 | | 2.738 | 0.075 | 3.5 |
| $K_2SO_4$ | 1.386 | | 2.475 | 0.021 | 0.7 |
| $Li_2SO_4$ | 1.138 | | 2.177 | 0.051 | 3.0 |
| $Na_2CrO_4$ | 1.091 | | 2.443 | 0.051 | 4.0 |
| $Na_2$ Fumarate | 1.259 | | 1.770 | 0.041 | 2.0 |
| $Na_2$ Maleate | 1.202 | | 2.699 | 0.075 | 3.0 |
| $Na_2SO_4$ | 0.988 | | 3.273 | 0.090 | 4.0 |
| $Na_2S_2O_3$ | 1.071 | | 2.709 | 0.064 | 3.5 |
| $(NH_4)_2SO_4$ | 1.006 | | 3.477 | 0.118 | 4.0 |
| $Rb_2SO_4$ | 1.150 | | 2.743 | 0.052 | 1.8 |
| 1-3 Electrolytes | | | | | |
| $K_3Fe(CN)_6$ | 1.328 | | 4.996 | 0.101 | 1.4 |
| 1-4 Electrolytes | | | | | |
| $K_4Fe(CN)_6$ | 1.449 | | 9.448 | 0.146 | 0.9 |
| 2-1 Electrolytes | | | | | |
| $BaAc_2$ | 1.016 | | 0.997 | 0.128 | 3.5 |
| $BaBr_2$ | 1.267 | | 0.358 | 0.018 | 2.0 |
| $BaCl_2$ | 1.227 | | 0.585 | 0.029 | 1.8 |
| $Ba(ClO_4)_2$ | 1.305 | | 0.261 | 0.049 | 5.0 |
| $BaI_2$ | 1.354 | 0.028 | | 0.017 | 2.0 |
| $Ba(NO_3)_2$ | 1.435 | | 1.268 | 0.008 | 0.4 |
| $CaBr_2$ | 1.969 | | 0.171 | 0.495 | 6.0 |
| $CaCl_2$ | 1.701 | | 0.309 | 0.283 | 6.0 |
| $Ca(ClO_4)_2$ | 2.021 | | | 0.431 | 6.0 |
| $CaI_2$ | 1.419 | 0.131 | | 0.036 | 2.0 |
| $Ca(NO_3)_2$ | 1.108 | | 0.875 | 0.053 | 6.0 |
| $CdBr_2$ | 1.324 | | 3.164 | 0.294 | 4.0 |
| $CdCl_2$ | 1.052 | | 3.047 | 0.315 | 6.0 |
| $CdI_2$ | 1.780 | | 3.820 | 0.337 | 2.5 |
| $Cd(NO_3)_2$ | 1.176 | | 0.500 | 0.037 | 2.5 |
| $CoBr_2$ | 1.779 | | | 0.218 | 5.0 |
| $CoCl_2$ | 1.397 | | 0.194 | 0.046 | 4.0 |
| $CoI_2$ | 2.260 | | | 0.488 | 6.0 |
| $Co(NO_3)_2$ | 1.444 | | 0.296 | 0.113 | 5.0 |
| $CuCl_2$ | 1.033 | 0.425 | 1.217 | 0.069 | 6.0 |
| $Cu(NO_3)_2$ | 1.409 | | 0.416 | 0.117 | 6.0 |
| $FeCl_2$ | 1.319 | | 0.255 | 0.011 | 2.0 |
| $MgAc_2$ | 1.192 | | 0.946 | 0.059 | 4.0 |
| $MgBr_2$ | 1.941 | | | 0.347 | 5.0 |
| $MgCl_2$ | 1.745 | | 0.144 | 0.275 | 5.0 |
| $Mg(ClO_4)_2$ | 1.988 | 0.162 | | 0.303 | 4.0 |
| $MgI_2$ | 2.237 | | | 0.470 | 5.0 |
| $Mg(NO_3)_2$ | 1.493 | | 0.198 | 0.140 | 5.0 |
| $MnCl_2$ | 1.273 | | 0.343 | 0.020 | 6.0 |
| $NiCl_2$ | 1.533 | | 0.189 | 0.123 | 5.0 |
| $Pb(ClO_4)_2$ | 1.549 | | 0.236 | 0.184 | 6.0 |
| $Pb(NO_3)_2$ | 1.129 | | 1.964 | 0.083 | 2.0 |

TABLE 3-continued

Results of Fit for Molality Scale Mean Ionic Activity Coefficient Data of Aqueous Electrolytes at 298.15K (Data from Robinson and Stokes, 1970)

| | E | Y− | Y+ | $\sigma$ | max. molality |
|---|---|---|---|---|---|
| SrBr$_2$ | 1.330 | | 0.183 | 0.023 | 2.0 |
| SrCl$_2$ | 1.401 | | 0.357 | 0.082 | 4.0 |
| Sr(ClO$_4$)$_2$ | 1.742 | | 0.034 | 0.261 | 6.0 |
| SrI$_2$ | 1.384 | 0.076 | | 0.030 | 2.0 |
| Sr(NO$_3$)$_2$ | 0.978 | | 1.250 | 0.091 | 4.0 |
| UO$_2$Cl$_2$ | 1.277 | | 0.024 | 0.017 | 3.0 |
| UO$_2$(ClO$_4$)$_2$ | 2.854 | | | 0.883 | 5.5 |
| UO$_2$(NO$_3$)$_2$ | 1.392 | 0.372 | 0.490 | 0.036 | 5.5 |
| ZnBr$_2$ | 0.906 | | 0.337 | 0.088 | 6.0 |
| ZnCl$_2$ | 0.953 | | 0.971 | 0.065 | 6.0 |
| Zn(ClO$_4$)$_2$ | 2.045 | 0.130 | | 0.318 | 4.0 |
| ZnI$_2$ | 0.868 | 0.132 | | 0.116 | 6.0 |
| Zn(NO$_3$)$_2$ | 1.518 | | 0.214 | 0.176 | 6.0 |
| 2-2 Electrolytes | | | | | |
| BeSO$_4$ | 1.376 | | 4.077 | 0.233 | 4.0 |
| MgSO$_4$ | 1.380 | | 4.206 | 0.238 | 3.0 |
| MnSO$_4$ | 1.287 | | 4.460 | 0.271 | 4.0 |
| NiSO$_4$ | 1.398 | | 4.381 | 0.220 | 2.5 |
| CuSO$_4$ | 1.587 | | 4.114 | 0.154 | 1.4 |
| ZnSO$_4$ | 1.339 | | 4.417 | 0.242 | 3.5 |
| CdSO$_4$ | 1.295 | | 4.547 | 0.271 | 3.5 |
| UO$_2$SO$_4$ | 1.215 | | 4.528 | 0.309 | 6.0 |
| 3-1 Electrolytes | | | | | |
| AlCl$_3$ | 1.730 | | 0.579 | 0.087 | 1.8 |
| CeCl$_3$ | 1.562 | | 0.883 | 0.047 | 1.8 |
| CrCl$_3$ | 1.589 | | 0.641 | 0.022 | 1.2 |
| Cr(NO$_3$)$_3$ | 1.551 | | 0.761 | 0.036 | 1.4 |
| EuCl$_3$ | 1.586 | | 0.820 | 0.049 | 2.0 |
| LaCl$_3$ | 1.553 | | 0.877 | 0.042 | 2.0 |
| NdCl$_3$ | 1.575 | | 0.882 | 0.045 | 2.0 |
| PrCl$_3$ | 1.562 | | 0.892 | 0.042 | 2.0 |
| ScCl$_3$ | 1.636 | | 0.709 | 0.041 | 1.8 |
| SmCl$_3$ | 1.581 | | 0.843 | 0.046 | 2.0 |
| YCl$_3$ | 1.629 | | 0.807 | 0.057 | 2.0 |
| 3-2 Electrolytes | | | | | |
| Al$_2$(SO$_4$)$_3$ | 1.354 | | 4.886 | 0.222 | 1.0 |
| Cr$_2$(SO$_4$)$_3$ | 1.257 | | 4.549 | 0.218 | 1.2 |
| 4-1 Electrolytes | | | | | |
| Th(NO$_3$)$_4$ | 1.273 | | 1.251 | 0.056 | 5.0 |

[1] $\sigma$ is defined to be $$\left[\sum_i^N \left(\frac{\gamma_{\pm i}^{*exp} - \gamma_{\pm i}^{*cal}}{\gamma_{\pm i}^{*exp}}\right)^2 / N\right]^{1/2}$$

where $\gamma_\pm^*$ is the mean ionic acitivity acoefficient of electrolyte and N is the number of data used in correlations

TABLE 4 eNRTL-SAC Model Parameters for Solutes

| solute | no. of solvents | X | Y− | Y+ | Z | E | ln K$_{sp}$ | $\sigma$[4] |
|---|---|---|---|---|---|---|---|---|
| benzoic acid[1] | 26 | 0.494 | | 0.336 | 0.468 | | −1.714 | 0.292 |
| salicylic acid[1] | 18 | 0.726 | 0.176 | | 0.749 | | −1.624 | 0.774 |
| p-aminobenzoic acid[1] | 19 | 0.552 | 0.423 | 0.594 | 0.881 | | −3.348 | 1.206 |
| Ibuprofen[1] | 19 | 1.038 | 0.051 | 0.028 | 0.318 | | −1.423 | 1.055 |
| Diclofenac[1] | 16 | 0.158 | | 1.678 | 0.451 | | −3.560 | 0.991 |
| sodium chloride[2] | 10 | | | 1.444 | | 0.994 | −6.252 | 0.783 |
| sodium acetate[2] | 5 | | | 1.417 | | 0.521 | −6.355 | 0.241 |
| sodium benzoate[2] | 10 | | 0.750 | 1.685 | 2.201 | 0.539 | −7.312 | 0.493 |
| sodium salicylate[2] | 13 | | | 0.845 | 2.417 | 0.090 | −4.889 | 0.771 |
| sodium p-aminobenzoate[2] | 12 | | | 2.299 | 2.387 | 0.192 | −8.293 | 1.258 |
| sodium ibuprofen[2] | 11 | 1.819 | 1.743 | | 2.362 | 0.150 | −17.844 | 0.886 |
| sodium diclofenac[2] | 10 | 0.409 | | 3.558 | 3.486 | 0.161 | −14.202 | 0.858 |
| sodium chloride[3] | 10 | | | 1.060 | 2.200 | | −3.540 | 0.923 |
| sodium acetate[3] | 5 | | | 0.249 | 0.679 | | −2.277 | 0.281 |
| sodium benzoate[3] | 10 | | | 0.179 | 1.825 | | −2.978 | 0.699 |
| sodium salicylate[3] | 13 | | | 0.373 | 1.572 | | −2.153 | 1.058 |
| sodium p-aminobenzoate[3] | 12 | | 0.125 | 0.649 | 1.895 | | −3.247 | 1.904 |
| sodium ibuprofen[3] | 11 | 0.270 | 0.394 | | 0.823 | | −2.364 | 1.685 |
| sodium diclofenac[3] | 10 | 0.454 | | 0.124 | 2.493 | | −4.405 | 1.473 |

[1] nonelectrolytes
[2] electrolytes
[3] treated as nonelectrolytes
[4] $\sigma$ is defined to be $$\left(\sum_i^N (\ln x_i^{exp} - \ln x_i^{cal})^2 / N\right)^{1/2}$$

where x is the solubility of solute, i.e., mole fraction (note that mass fraction for sodium chloride and sodium acetate), and N is the number of data used in correlations.

CONCLUSIONS

The NRTL-SAC model of related U.S. patent application Ser. No. 10/785,925 (by assignee), a practical thermodynamic framework for solubility modeling of organic nonelectrolytes, has been extended for electrolytes. The electrolyte NRTL-SAC model 20 of the present invention requires only one additional component-specific electrolyte parameter over the three types of molecular parameters associated with the NRTL-SAC model. For solute molecules, these parameters are identified from solubility measurements of the solute in a few representative solvents, i.e., hydrophobic, hydrophilic and polar solvents. While scarcity of public literature solubility data on organic electrolytes has hampered extensive testing, Applicants have shown the extended model to be a promising tool for qualitative correlation and estimation of solubility of electrolyte systems including systems with large, complex organic electrolytes.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of manufacturing a chemical compound that includes at least one electrolyte, the method comprising:
   a) modeling at least one physical property including activity coefficient, vapor pressure, solubility, boiling point, freezing point, and octanol/water partition coefficient of a mixture of the at least one electrolyte dissolved in at least one solvent by the computer implemented steps of:
      i) determining a conceptual segment, instead of a molecular structural segment, for the at least one electrolyte dissolved in the at least one solvent, the conceptual segment being determined from in-mixture behavior of the at least one electrolyte, including for the at least one electrolyte, (a) identifying at least a conceptual electrolyte segment and any other conceptual segment as one of a hydrophobic segment, a hydrophilic segment, or a polar segment, wherein a representation of the at least one electrolyte includes the conceptual electrolyte segment for the electrolyte, and (b) defining at least a segment number for the conceptual electrolyte segment, the segment number being based on experimental data and being one of carried in a databank of molecular descriptors of known electrolytes or obtained using a calculator of molecular descriptors of unknown electrolytes by best fit of experimental phase equilibrium data for binary systems of unknown electrolytes and reference electrolytes;
      ii) using the determined conceptual electrolyte segment, computing at least one physical property including activity coefficient, vapor pressure, solubility, boiling point, freezing point, and octanol/water partition coefficient of the mixture by determining an activity coefficient of the at least one electrolyte, the activity coefficient being formed of at least a local composition interaction contribution to the activity coefficient for the at least one electrolyte based on the determined conceptual segments; and
      iii) providing an analysis of the computed physical property, wherein the analysis forms a model of the at least one physical property of the mixture; and
   b) using the formed model in implementing a manufacturing process for manufacturing the chemical compound, said manufacturing process including the at least one electrolyte dissolved in the at least one solvent in at least one step in manufacturing the chemical compound, such that the chemical compound as manufactured has the at least one physical property of the mixture determined by the model.

2. The method of manufacturing a chemical compound of claim 1, wherein the chemical compound is any of a pharmaceutical compound, a nonpolymeric compound, a polymer, an oligomer, an inorganic compound and an organic compound.

3. The method of manufacturing a chemical compound of claim 1, further including selecting the at least one electrolyte by using the model.

4. The method of manufacturing a chemical compound of claim 1, wherein the conceptual electrolyte segment includes a a cationic segment number and an anionic segment number.

5. The method of manufacturing a chemical compound of claim 4, wherein the cationic segment number and the anionic segment number are represented by the following formulas:

$$r_{c,C} = r_{e,CA} Z_C \text{ and } r_{a,A} = r_{e,CA} Z_A,$$

wherein:
   the mixture includes one single electrolyte;
   $r_e$ is the electrolyte segment number, $r_c$ is the cationic segment number,
   $r_a$ is the anionic segment number, where $r_c$ and $r_a$ satisfy electroneutrality;
   CA is an electrolyte, wherein C is a cation, and A is an anion; and
   $Z_C$ is the charge number for C, and $Z_A$ is the charge number for A.

6. The method of manufacturing a chemical compound of claim 4, wherein the cationic segment number and the anionic segment number are represented by the following formulas:

$$r_{c,C} = \Sigma_A r_{e,CA} Z_C (x_A Z_A / \Sigma_{A'} x_{A'} Z_{A'}) \text{ and}$$

$$r_{a,A} = \Sigma_{C'} r_{e,CA} Z_A (x_C Z_C / \Sigma_{C'} x_{C'} Z_{C'}),$$

wherein:
   the mixture includes multiple electrolytes;
   $r_e$ is the segment number, $r_c$ is the cationic segment number,
   $r_a$ is the anionic segment number, where $r_c$ and $r_a$ satisfy electroneutrality;
   CA is an electrolyte, wherein C is a cation, and A is an anion;
   C'A' is other electrolyte(s), wherein C' is a cation and A' is an anion;
   $Z_C$ is a charge number for C, and $Z_A$ is a charge number for A;
   $Z_{C'}$ is a charge number for other C', and $Z_{A'}$ is a charge number for other A';
   $x_A$ is a mole fraction of A, and $x_C$ is a mole fraction of C; and
   $x_{A'}$ is a mole fraction of A', and $x_{C'}$ is a mole fraction of C'.

7. The method of manufacturing a chemical compound of claim 1, wherein the computed physical property includes lipophilicity of the electrolyte.

8. The method of manufacturing a chemical compound of claim 1, wherein solubility is represented by the following formula:

$$K_{sp}(T) = \Pi_C x_C^{v_C,SAT} \gamma^{*v_C,SAT}_C \Pi_A x_A^{v_A,SAT} \gamma^{*v_A,SAT}_A \Pi_M x_M^{v_M,SAT} \gamma_M^{SAT},$$

wherein:
   $K_{sp}$ is the solubility product constant for the electrolyte,

T is the temperature of the mixture, $x_C^{v_C SAT}$ is the mole fraction of a cation derived from the electrolyte at saturation point of the electrolyte, $x_A^{v_A SAT}$ is the mole fraction of an anion derived from the electrolyte at saturation point of the electrolyte, $x_M^{v_M SAT}$ is the mole fraction of a neutral molecule derived from the electrolyte at saturation point of the electrolyte, $\gamma_C^{*v_C,SAT}$ is the activity coefficient of a cation derived from the electrolyte at the saturation concentration;

$\gamma_A^{*v_A,SAT}$ is the activity coefficient of an anion derived from the electrolyte at the saturation concentration;

$\gamma_M^{*v_M,SAT}$ is the activity coefficient of a neutral molecule derived from the electrolyte at the saturation concentration;

C is the cation, A is the anion, M is solvent or solute molecule, T is the temperature of the mixture, $\gamma^*$ is the unsymmetric activity coefficient of a species in solution, SAT is saturation concentration, $\upsilon_C$ is the cationic stoichiometric coefficient, $\upsilon_A$ is the anionic stoichiometric coefficient, and $\upsilon_M$ is the neutral molecule stoichiometric coefficient.

9. The method of manufacturing a chemical compound of claim 1, wherein the electrolyte is symmetrical or unsymmetrical.

10. The method of manufacturing a chemical compound of claim 1, wherein the electrolyte is univalent or multivalent.

11. The method of manufacturing a chemical compound of claim 1, wherein the electrolyte includes two or more ionic species.

12. The method of manufacturing a chemical compound of claim 1, wherein the solvent is water, and the step of computing at least one physical property includes calculating:

$$\ln \gamma_I^* = \ln \gamma_I^{*lc} + \ln \gamma_I^{*PDH} + \ln \gamma_I^{*FH},$$

wherein:
I is the ionic specie;
$\ln \gamma_I^*$ is the logarithm of an activity coefficient of I;
$\ln \gamma_I^{*lc}$ is the local composition term of I;
$\ln \gamma_I^{*PDH}$ is the Pitzer-Debye-Hückel term of I; and
$\ln \gamma_I^{*FH}$ is the Flory-Huggins term of I.

13. The method of manufacturing a chemical compound of claim 1, wherein the one or more solvents include mixed-solvent solutions, and the step of computing at least one physical property including calculating:

$$\ln \gamma_I^* = \ln \gamma_I^{*lc} + \ln \gamma_I^{*PDH} + \ln \gamma_I^{*FH} + \Delta \ln \gamma_I^{Born},$$

wherein:
I is the ionic specie;
$\ln \gamma_I^*$ is the logarithm of an activity coefficient of I;
$\ln \gamma_I^{*lc}$ is the local interaction contribution of I;
$\ln \gamma_I^{*PDH}$ is the Pitzer-Debye-Hückel term of I;
$\ln \gamma_I^{*FH}$ is the Flory-Huggins term of I; and
$\Delta \ln \gamma_I^{Born}$ is the Born term of I.

* * * * *